(12) United States Patent
Epstein et al.

(10) Patent No.: US 9,522,958 B2
(45) Date of Patent: Dec. 20, 2016

(54) CANCER TARGETED INNATE IMMUNITY

(75) Inventors: Alan L. Epstein, La Canada, CA (US); Leslie A. Khawli, Arcadia, CA (US)

(73) Assignee: University of Southern California, Los Angeles, CA (US)

( * ) Notice: Subject to any disclaimer, the term of this patent is extended or adjusted under 35 U.S.C. 154(b) by 0 days.

(21) Appl. No.: 13/228,317

(22) Filed: Sep. 8, 2011

(65) Prior Publication Data

US 2012/0076804 A1   Mar. 29, 2012

Related U.S. Application Data

(62) Division of application No. 11/269,123, filed on Nov. 8, 2005, now abandoned.

(60) Provisional application No. 60/626,829, filed on Nov. 9, 2004.

(51) Int. Cl.
*C07K 16/00* (2006.01)
*C07K 16/30* (2006.01)
*A61K 47/48* (2006.01)

(52) U.S. Cl.
CPC ......... *C07K 16/30* (2013.01); *A61K 47/48092* (2013.01); *A61K 47/48569* (2013.01); *C07K 2317/80* (2013.01)

(58) Field of Classification Search
USPC ........................................... 530/391.7, 391.9
See application file for complete search history.

(56) References Cited

U.S. PATENT DOCUMENTS

| | | | |
|---|---|---|---|
| 4,816,567 | A | 3/1989 | Cabilly et al. |
| 4,956,778 | A | 9/1990 | Naito |
| 5,091,513 | A | 2/1992 | Huston et al. |
| 5,116,943 | A | 5/1992 | Koths et al. |
| 5,132,405 | A | 7/1992 | Huston et al. |
| 5,306,809 | A | 4/1994 | Boon et al. |
| 5,530,101 | A | 6/1996 | Queen et al. |
| 5,565,332 | A | 10/1996 | Hoogenboom et al. |
| 5,767,071 | A | 6/1998 | Palladino et al. |
| 5,780,426 | A | 7/1998 | Palladino et al. |
| 6,013,625 | A | 1/2000 | Pierschbacher et al. |
| 6,331,415 | B1 | 12/2001 | Cabilly et al. |
| 6,365,619 | B1 | 4/2002 | Shi |
| 6,827,925 | B1 | 12/2004 | Williams et al. |
| 2003/0149246 | A1* | 8/2003 | Russell ............... 530/391.1 |
| 2004/0053880 | A1* | 3/2004 | Krieg ...................... 514/44 |

FOREIGN PATENT DOCUMENTS

WO   WO-01/97843   12/2001

OTHER PUBLICATIONS

Agrawal et al., Medicinal chemistry and therapeutic potential of CpG DNA, TRENDS in Molecular Medicine 8(3):114-121 (2002).
Betting et al., Intratumoral but not systemic delivery of CpG oligodeoxynucleotide augments the efficacy of anti-CD20 monoclonal antibody therapy against B cell lymphoma, J Immunother 00(00): 1-10 (2009).
Biela et al., Chimeric TNT-3/human β-glucuronidase fusion proteins for antibody-directed enzyme prodrug therapy (ADEPT), Cancer Biother Radiopharm, 18(3):339-353 (2003).
European Communication pursuant to Article 94(3) EPC dated Jan. 14, 2011 in European Application No. 05851410.
European Summons to attend oral proceedings pursuant to Rule 115(1) EPC dated Mar. 5, 2012 in European Application No. 05851410.
Gray et al., CpG-B ODNs potently induce low levels of IFN-αβ and induce IFN-αβ-dependent MHC-I cross-presentation in DCs as effectively as CpG-A and CpG-C ODNs, Journal of Leukocyte Biology 81:1075-1085 (2007).
Gurunathan et al., DNA Vaccines: Immunology, application, and optimization, Annu. Rev. Immunol. 18:927-974 (2000).
Hu et al., Comparison of three different targeted tissue factor fusion proteins for inducing tumor vessel thrombosis, Cancer Res., 63(16):5046-5053, (2003).
Krieg, CpG Motifs in Bacterial DNA and Their Immune Effects, Annu. Ref. Immunol. 20:709-760 (2002).
Martinson et al., Impact of class A, B and C CpG-oligodeoxynucleotides on in vitro activation of innate immune cells in human immunodeficiency virus-1 infected individuals, Immunology 120: 526-535 (2006).
Palma et al., Improved systemic phamacokinetics, biodistribution, and antitumor activity of CpG oligodeoxynucleotides complexed to endogenous antibodies in vivo, Journal of Controlled Release 120: 95-103 (2007).
Sadun et al., Fc-mOX40L Fusion Protein Produces Complete Remission and Enhanced Survival in 2 Murine Tumor Models, J Immunother 31(3): 235-245 (2008).
Sharma et al., Systemic targeting of CpG-ODN to the tumor microenvironment with anti-neu-CpG hybrid molecule and T regulatory cell depletion induces memory responses in BALB-neuT tolerant mice, Cancer Res., 68(18):7530-7540, 2008.
Switaj et al., CpG immunostimulatory oligodeoxynucleotide 1826 enhances antitumor effect of interleukin 12 gene-modified tumor vaccine in a melanoma model in mice, Clinical Cancer Research 10:4165-4175 (2004).
Wooldridge et al., CpG DNA and cancer immunotherapy: orchestrating the antitumor immune response, Curr Opin Oncol 15: 440-445 (2003).
Altschul et al., "Basic Local Alignment Search Tool," J. Mol. Biol. 215:403-410 (1990).
Altschul et al., Gapped BLAST and PSI-BLAST: a new generation of protein database search programs; Nucl. Acids Res., 25:3389-3402 (1977).
Baines et al., Immune-mediated Tumor Regression Induced by CpG-containing Oligodeoxynucleotides; Clin. Cancer Res., 9:2693-2700 (2003).
Berghella et al., Bcl-2 and Drugs Used in the Treatment of Cancer: New Strategies of Biotherapy which should not be Underestimated; Cancer Biother. & Radiopharm., 13:225-237 (1998).

(Continued)

*Primary Examiner* — Yan Xiao

(74) *Attorney, Agent, or Firm* — Foley & Lardner LLP; Antoinette F. Konski

(57) ABSTRACT

Provided is a cancer therapeutic agent comprising a cancer targeting molecule linked to a CpG oligodeoxynucleotide. Also provided are methods of reducing the size of a tumor or inhibiting the growth of cancer cells in an individual or inhibiting the development of metastatic cancer, comprising administering an effective amount of the cancer therapeutic agent. The methods may also include reducing immunoregulatory T cell activity in the individual.

12 Claims, 3 Drawing Sheets

(56) References Cited

OTHER PUBLICATIONS

Blattler et al., New Heterobifunctional Protein Cross-Linking Reagent That Forms an Acid-Labile Link; Biochem., 24:1517-1524 (1985).

Chang et al., The Discovery of Small Molecule Carbamates as Potent Dual a4β1/ a4β7 Integrin Antagonists; Bioorganic & Medicinal Chem. Lett., 12:159-163 (2002).

Chen et al., Tumor Necrosis Treatment of ME-180 Human Cervical Carcinoma Model with 131I-Labeled TNT-1 Monoclonal Antibody; Cancer Res., 49:4578-4585 (1989).

Cooper et al., Digging for innate immunity since Darwin and Metchnikoff; BioEssays, 24:319-333 (2002).

Cooper, The Biology of Cell Death in Tumours; Cell Tissue Kinet., 6:87-95 (1973).

Davila E. et al. Generation of Antitumor Immunity by Cytotoxic T Lymphocyte Epitope Peptide Vaccination,CpG-oligonulceotide Adjuvant.,and CTLA-4 Blockade. Cancer Research. Jun. 15, 2003,vol. 63, 3281-3288.

Dy et al., Novel Targets for Lung cancer Therapy: Part I; J. Clin. Oncol. 20: 2881-2894 (2002).

Epstein et al, A Novel Method for the Detection of Necrotic Lesions in Human Cancers, Cancer Res., vol. 48, pp. 5842-5848, 1988.

Francis et al., PEGylation of cytokine and other therapeutic proteins and peptides: the importance of biological optimization of coupling techniques;. Int. J. Hematol., 68:1-18 (1998).

Frankel et al., The Rapid Determination of Binding Constants for Antiviral Antibodies by a Radioimmunoassay. An Analysis of the Interaction between Hybridoma Proteins and Influenza Virus; Mol. Immunol., 16:101-106 (1979).

Goldenberg D.M. Scientific American, Mar./Apr. 1994, pp. 64-73.

Gursel et al., Differential and competitive activation of human immune cells by distinct classes of CpG oligodeoxynucleotide. J. Leukocyte Biol., 71:813-820 (2002).

Hank et al. Clinical Cancer Research, 2:1951-1959, Dec. 1996.

Hemmi et al., A Toll-like receptor recognizes bacterial DNA; Nature, 208:740-745 (2000).

Henikoff et al., "Amino acid substitution matrices from protein blocks", Proc. Natl. Acad. Sci., (1992), 89:10915-10919.

Hornick et al., A New Chemically Modified Chimeric TNT-3 Monoclonal Antibody Directed Against DNA for the Radioimmunotherapy for Solid Tumors; Cancer Biother. & Radiopharm., 13:255-268 (1998).

Hornick et al., Pretreatment with a Monoclonal Antibody/Interleukin-2 Fusion Protein Directed against DNA Enhances the Delivery of Therapeutic Molecules to Solid Tumors; Clin. Cancer Res., 5:51-60 (1999).

Huston et al., Protein engineering of antibody binding sites: Recovery of specific activity in an anti-digoxin single-chain Fv analogue produced in *Escherichia coli*.; Proc. Nat. Acad. Sci., USA, 85:5879-5883 (1988).

International Search Report for PCT Application No. PCT/US05/40315.

Ishii et al., Antitumor Therapy with Bacterial DNA and Toxin: Complete Regression of Established Tumor Induced by Liposomal CpG Oligodeoxynucleotides plus Interleukin-13 Cytotoxin; Clin. Cancer Res., 9:6516-6522 (2003).

Jakob et al., Activation of Cutaneous Dendritic Cells by CpG-Containing Oligodeoxynucleotides: A Role for Dendritic Cells in the Augmentation of Th1 Responses by Immunostimulatory DNA1;J. Immunol., (1998) 161:3042-3049.

June, C.H., Can't Get Any Help? New Approaches for Adoptive Immunotherapy of Cancer; J. Immunother., 24(5): 389-391 (2001).

Kandimalla et al, "Conjugation of ligands and 5'-end of CpG DNA affects immunostimulatory activity", Bioconjugate Chemistry, ACS, Washington D.C., vol. 13, pp. 966-974, Jan. 1, 2002.

Kandimalla et al., Conjugation of Ligands at the 5 19-End of CpG DNA Affects Immunostimulatory Activity; Bioconjug. Chem., 13:966-974 (2002).

Karlin et al., Applications and statistics for multiple high-scoring segments in molecular sequences; Proc. Natl. Acad. Sci., USA, 90:5873 (1993).

Katre et al., Immunogenicitiy of Recombinant IL-2 Modified by Covalent Attachment of Polyethylene Glycol; J. Immunol., 144:209-213 (1990).

Khawli et al. Improved Tumor Localization and Radioimaging with Chemically Modified Monoclonal Antibodies; Cancer Biother. & Radiopharm., 11:203-215 (1996).

Khawli et al., "Effect of Seven New Vasoactive Immunoconjugates on the Enhancement of Monoclonal Antibody Uptake in Tumors," Cancer 73:824-831 (1994).

Klinman et al., CpG motifs present in bacterial DNA rapidly induce lymphocytes to secrete interleukin 6, interleukin 12, and interferon ?; Proc. Natl. Acad. Sci., 93:2879-2883 (1996).

Klinman, D.M., Immunotherapeutic Uses of CpG Oligodeoxynucleotides; Nature Rev. Immunol., 4:249-258 (2004).

Krieg et al., CpG motifs in bacterial DNA trigger direct B-cell activation; Nature, 374:546-549 (1995).

Krieg, A.M., CpG motifs: the active ingredient in bacterial extracts?; Nature Med., 9:831-835 (2003).

Krug et al., Identification of CpG oligonucleotide sequences with high induction of IFN-a/β in plasmacytoid dendritic cells ; Eur. J. Immunol., 31:2154-2163 (2001).

Kuijpers et al., Bioconjugate Chemistry, 4:94-102, 1993.

Latz et al., TLR9 signals after translocating from the ER to CpG DNA in the lysosome; Nature Immunol., 5:190-198 (2004).

Lawton et al., Novel therapeutic strategies based on toll-like receptor signaling; Current Opin. Chem. Biol., 7:446-451 (2003).

LeBerthon et al., Enhanced Tumor Uptake of Macromolecules Induced by a Novel Vasoactive Interleukin 2 Immunoconjugate; Cancer Res., 51:2694-2698 (1991).

Li et al., Complete regression of experimental solid tumors by combination LEC/chTNT-3 immunotherapy and CD25+ T-cell division, Cancer Research, 63:8384-8392, 2003.

Li et al., LEC/chTNT-3 Fusion Protein for the Immunotherapy of Experimental Solid Tumors; J. Immunother., 26:320-331 (2003).

Lin et al., Specific and Dual Antagonists of a41β1 and a4β7 Integrins; Bioorganic & Medicinal Chem. Lett., 12:133-136 (2002).

Lipford et al., CpG-containing synthetic oligonucleotides promote B and cytotoxic T cell responses to protein antigen: a new class of vaccine adjuvants; Eur. J. Immunol., 27:2340-2344 (1997).

Lum et al., Immune Modulation in Cancer Patients After Adoptive Transfer of Anti-CD3/anti-CD28-Costimulated T Cells—Phase 1 Clinical Trial; J Immunother., 24:408-419 (2001).

Marcucci Fabrizio et al, Active targeting with particulate drug carriers in tumor therapy: fundametals and recent progress, Drug Discovery Today, Mar. 1, 2004, vol. 9,. No. 5, pp. 219-228.

Medzhitov et al., Innate Immunity: impact on the adaptive immune response; Current Opin. Immunol., 9:4-9 (1997).

Meiser et al., Chimeric Monoclonal CD4 Antibody—A Novel Immunosuppressant for Clinical Heart Transplantation; Transplantation., 58(4): 419-23 (1994).

Messina et al, Stimulation of in vitro Murine Lymphocyte Proliferation by Bacterial DNA; J. Immunol., 147:1759-1764 (1991).

Milas et al., CpG Oligodeoxynucleotide Enhances Tumor Response to Radiation; Cancer Res., 64:5074-5077 (2004).

Miller et al., Immunologic and Biochemical Analysis of TNT-1 and TNT-2 Monoclonal Antibody Binding to Histones; Hybridoma, 12:689-698 (1993).

Mocellin et al., Adjuvant immunotherapy for solid tumors: from promise to clinical application; Cancer Immunol. & Immunother., 51: 583-595 (2002).

Myers et al., The effects of aromatic and aliphatic maleimide crosslinkers on anti-CD5 ricin immunotoxins; J. Immunol. Methods, 121:129-142 (1989).

Needleman et al., A General Method Applicable to the Serch for Similarities in the Amino Acid Sequence of Two Proteins; J. Mol. Biol., 48:443 (1970).

Office Action dated Jan. 21, 2010 for U.S. Appl. No. 11/269,123.

Office Action dated Feb. 10, 2009 for U.S. Appl. No. 11/269,123.

Office Action dated Apr. 12, 2010 for EP Application No. 05851410.0.

(56) References Cited

OTHER PUBLICATIONS

Office Action on 075405-0903 DTD Oct. 9, 2007.
Ozinsky et al., The repertoire for pattern recognition of pathogens by the innate immune system is defined by the cooperation between Toll-like receptors; Proc. Natl. Acad. Sci., 97:13766-13771 (2000).
Park et al., Targeting and Blocking B7 Costimulatory Molecules on Antigen-Presenting Cells Using CTLA4lg-Conjugated Liposomes: In Vitro Characterization and in Vivo Factors Affecting Biodistribution; Pharm. Res., 20(8):1239-48 (2003).
Pearson et al., Improved tools for biological sequence comparison; Proc. Nat'l. Acad. Sci. USA, 85:2444 (1988).
Porkka et al., A fragment of the HMGN2 protein homes to the nuclei of tumor cells and tumor endothelial cells in vivo; Proc. Natl. Acad. Sci., USA, 99(11): 7444-7449. (2002).
Rothenfusser et al., CpG-A and CpG-B oligonucleotides differentially enhance human peptide-specific primary and memory CD8+ T-cell responses in vitro; Blood, 103:2162-2169 (2004).
Schraa et al., Endothelial cells internalize and degrade RGD-modified proteins developed for tumor vasculature targeting; Control Release, 83(2): 241-51 (2002).
Sen et al., The critical DNA flanking sequences of a CpG oligodeoxynucleotide, but not the 6 base CpG motif, can be replaced with RNA without quantitative or qualitative changes in Toll-like receptor 9-mediated activity; Cell Immunol. 232(1-2):64-74 (2004).
Seo et al., Depletion of IL-10- and TGF-β-Producing Regulatory ?d T Cells by Administering a Daunomycin-Conjugated Specific Monoclonal Antibody in Early Tumor Lesions Augments the Activity of CTLs and NK Cells; J. Immunol., 163:242-249 (1999).
Sharifi et al., Characterization of a Phage Display-Derived Human Monoclonal Antibody (NHS76) Counterpart to Chimeric TNT-1 Directed against Necrotic Regions of Solid Tumors; Hybridoma and Hybridomics, 20:305-312 (2001).
Sharifi et al., Improving monoclonal antibody pharmacokinetics via chemical modification; Q.J.Nucl.Med., 42:242-249 (1998).
Smith et al., Comparison of Biosequences; Adv. Appl. Math., 2:482 (1981).
Stacey et al., Macrophage Activation by Immunostimulatory DNA ; Curr. Topics Microbiol. Immunol., 247:41-58 (2000).
Stein et al., Physicochemical properties of phosphorothioate oligodeoxynucleotides; Nucleic Acids Res., 16:3209-3221 (1988).
Supplementary EP Search Report dated Jan. 26, 2009 for EP 05851410.

Tauszig et al., Toll-related receptors and the control of antimicrobial peptide expression in *Drosophila*; Proc. Natl. Acad. Sci., USA, 97:10520-10525 (2000).
Tokunaga et al., Antitumor Activity of Deoxyribonucleic Acid Fraction From *Mycobacterium bovis* BCG. I. Isolation, Physicochemical Characterization and Antitumor Actuvuty; JNCI, 72:955-962 (1984).
Tone et al., Mouse glucocorticoid-induced tumor necrosis factor receptor ligand is costimulatory for T cells; Proc. Natl. Acad. Sci. 100:15059-15064 (2003).
Ulevitch R.J., Therapeutics Targeting the Innate Immune System; Nature Rev. Immunol., 4:512-520 (2004).
US Final Office Action for U.S. Appl. No. 11/269,123, dated Dec. 8, 2010.
US Office Action dated Jul. 20, 2010 for U.S. Appl. No. 11/269,123.
US Office Action on 075405-0903 DTD Aug. 6, 2008.
US Office Action on 075405-0903 DTD Jan. 21, 2010.
Verthelyi et al., Human Peripheral Blood Cells Differentially Recognize and Respond to Two Distinct CpG Motifs; J. Immunol., 166:2372-2377 (2001).
Vollmer et al., Characterization of three CpG oligodeoxynucleotide classes with distinct immunostimulatory activities; Eur. J. Immunol., 34:252-262 (2004).
Weiner G.J., The immunobiology and clinical potential of immunostimulatory CpG oligodeoxynucleotides; J. Leukocyte Biol., 68:445-463 (2000).
Wiemann et al., Coley's Toxins, Tumor Necrosis Factor and Cancer Research: A Historical Perspective; Pharmacol. Ther., 64:529-564 (1994).
Wilcox et al., Ligation of CD137 receptor prevents and reverses established anergy of CD8+ cytolytic T lymphocytes in vivo; Blood, 103:177-184 (2004).
Wines et al., The IgC Fc Contains Distinct Fc Receptor (FcR) Binding Sites: The Leukocyte Receptors Fc?RI and Fc?RIIa Bind to a Region in the Fe Distinct from That Recognized by Neonatal FcR and Protein A; J. Immunol., 164(10):5313-8(2000).
Woolridge et al., Immunostimulatory Oligodeoxynucleotides containing CpG Motifs Enhance the Efficacy of Monoclonal Antibody Therapy of Lymphoma; Blood, 89:2994-2998, (1997).
Yang et al., Doxorubicin conjugated with a monoclonal antibody directed to a human melanoma-associated proteoglycan suppresses the growth of established tumor xenografts in nude mice; Proc. Natl. Acad. Sci., USA, 85:1189-1193 (1988).

\* cited by examiner

```
                           SEQUENCE LISTING

<160> NUMBER OF SEQ ID NOS: 30

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
tccatgacgt tcctgacgtt                                                  20

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
tctcccagcg tgcgccat                                                    18

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
tcgtcgtttt cggcgcgcgc cg                                               22

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
tccatgacgt tcctgatgct                                                  20

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
tcgtcgtttt gtcgttttgt cgtt                                             24

<210> SEQ ID NO 6
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 6
ggggtcaacg ttgaggggg                                              20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
gggggacgat cgtcgggggg                                             20

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
tcgtcgtttt cggcgcgcgc cg                                          22

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
tcgtcgtttt ccggcgcgcc gg                                          22

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
tcgtcgtttt cggcggccgc cg                                          22

<210> SEQ ID NO 11
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
tcgagcgttc tc                                                     12

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 12
ggtgcatcga tgcagggggg                                                    20

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
tcgtcgtttt gtcgttttct cgt                                                23

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
tccaatgagc ttcctgagtc t                                                  21

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
tccaggactt ctctcaggtt                                                    20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
tccatgaggt tcctgatgct                                                    20

<210> SEQ ID NO 17
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
tgacaacaca tttgagtgcc aat                                                23

<210> SEQ ID NO 18
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
cagcaacagc aaggcgaaa                                                      19

<210> SEQ ID NO 19
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
catcttctca aaattcgagt gacaa                                               25

<210> SEQ ID NO 20
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
acaggagaag ggacgccat                                                      19

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
ggttgccaag ccttatcgga                                                     20

<210> SEQ ID NO 22
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
tgacgtcact ggagttgtac gg                                                  22

<210> SEQ ID NO 23
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
agctactgta atgatcagtc aacg                                                24

<210> SEQ ID NO 24
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
gaaggctatc catctcctca gaaa                                          24

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
ctggacctgt gggttgttga c                                             21

<210> SEQ ID NO 26
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
tgggagtaga caaggtacaa ccc                                           23

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
gaagccctac agacgagctc a                                             21

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
acctgctcca ctgccttgct                                               20

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
ggttcatgtc atggatggtg c                                             21

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 30
agaggtcctt ttcaccagca                                                  20
```

CANCER TARGETED INNATE IMMUNITY

CROSS REFERENCE TO RELATED PATENT APPLICATIONS

This application is a divisional application of U.S. patent application Ser. No. 11/269,123 filed Nov. 8, 2005, which claims priority under 35 U.S.C. §119(e) to U.S. Application Ser. No. 60/626,829, filed Nov. 9, 2004, each of which are incorporated herein by reference in their entirety.

SEQUENCE LISTING

The instant application contains a Sequence Listing which has been submitted via EFS-Web and is hereby incorporated by reference in its entirety. Said ASCII copy, created on Feb. 14, 2006 is named 75450903.txt, and is 7,207 bytes in size.

BACKGROUND OF THE INVENTION

The invention relates to cancer therapeutic agents and methods for cancer therapy.

The following discussion of the background of the invention is merely provided to aid the reader in understanding the invention and is not admitted to describe or constitute prior art to the present invention.

Surgery, radiation therapy, and chemotherapy have been the standard accepted approaches for treatment of cancers including leukemia, solid tumors, and metastases. Immunotherapy (sometimes called biological therapy, biotherapy, or biological response modifier therapy), which uses the body's immune system, either directly or indirectly, to shrink or eradicate cancer has been studied for many years as an adjunct to conventional cancer therapy. It is believed that the human immune system is an untapped resource for cancer therapy and that effective treatment can be developed once the components of the immune system are properly harnessed. As key immunoregulatory molecules and signals of immunity are identified and prepared as therapeutic reagents, the clinical effectiveness of such reagents can be tested using well-known cancer models. Immunotherapeutic strategies include administration of vaccines, activated cells, antibodies, cytokines, chemokines, as well as small molecular inhibitors, anti-sense oligonucleotides, and gene therapy (Mocellin, et al., Cancer Immunol. & Immunother. (2002) 51: 583-595; Dy, et al., J. Clin. Oncol. (2002) 20: 2881-2894, 2002).

The growth and metastasis of tumors depends to a large extent on their capacity to evade host immune surveillance and overcome host defenses. Most tumors express antigens that can be recognized to a variable extent by the host immune system, but in many cases, the immune response is inadequate. Failure to elicit a strong activation of effector T-cells may result from the weak immunogenicity of tumor antigens or inappropriate or absent expression of co-stimulatory molecules by tumor cells. For most T-cells, proliferation and IL-2 production require a co-stimulatory signal during TCR engagement, otherwise, T-cells may enter a functionally unresponsive state, referred to as clonal anergy.

As part of the immune system, innate immunity provides an early first line defense to pathogenic organisms which is followed by antibody and cellular T cell responses characteristic of the adaptive immune system. Innate immunity is highly robust and utilizes specific cells such as macrophages, neutrophils/PMNs, dendritic cells, and NK cells which are effective in destroying and removing diseased tissues and cells (Cooper et al., BioEssays (2002) 24:319-333). Since the demonstration by Coley that tumors could be treated by intratumoral injections of pathogens (Wiemann and Stames (1994) Pharmacol. Ther. 64:529-564), investigators have wondered if the innate immune system could be harnessed for the treatment of human diseases (Ulevitch, Nature Rev. Immunol. (2004) 4:512-520). However, attempts to use the innate immune system for cancer immunotherapy have been limited in comparison to the adaptive immune system.

As described by Medzhitov and Janeway, (Current Opin. Immunol. (1997) 9:4-9) the innate immune system is directed to recognition of invariant molecular structures in pathogens that are distinct from self-antigens yet are found on a large number of infecting organisms. These microbial stimulators of innate immune responses include lipopolysaccharides and teichoic acids shared by all gram-negative and gram-positive bacteria, respectively, unmethylated CpG motifs characterized by bacterial but not mammalian DNA, double-stranded RNA as a structural signature of RNA viruses, and mannans which are conserved elements of yeast cell walls. None of these structures are encoded by host organisms and all are shared by large groups of pathogens due to their importance in structure and/or propagation of the infecting organism. Mammals have developed a set of receptors which recognize these microbial components. Unlike T- and B-cell receptors of the adaptive immune system, however, these innate system receptors are germline encoded (since they have arisen evolutionarily over time due to selection by pathogens at the population level) and are strategically expressed on cells that are the first to encounter pathogens during infection (Ozinsky, et al., PNAS (2000) 97:13766-13771).

CpG Oligodeoxynucleotides (ODNs) are synthetic oligonucleotides that are comprised of unmethylated CG dinucleotides, arranged in a specific sequence and framework known as CpG motifs (Tokunaga, et al., JNCI (1984) 72:955-962; Messina, et al, J. Immunol. (1991) 147:1759-1764; Krieg, et al, Nature (1995) 374:546-549). CpG motifs trigger the production of T-helper 1 and pro-inflammatory cytokines and stimulate the activation of professional antigen-presenting cells (APCs) including macrophages and dendritic cells (Klinman et al. PNAS (1996) 93:2879-2883). Unmethylated CpG ODNs behave as immune adjuvants which accelerate and enhance antigen-specific antibody responses and are now thought to play a large role in the effectiveness of Freund's Adjuvant and BCG (Krieg, Nature Med. (2003) 9:831-835). Recently, it was discovered that CpG ODNs interact with Toll-like receptor (TLR) 9 to trigger the maturation and functional activation of professional antigen presenting cells, B-cells, and natural killer cells (Hemmi, et al. Nature (2000) 208:740-745; Tauszig, et al, PNAS (2000) 97:10520-10525; Lawton and Ghosh Current Opin. Chem. Biol. (2003) 7:446-451). CpG ODNs are quickly internalized by immune cells, through a speculated pathway involving phophatidylinositol 3-kinases (PI3Ks), and interact with TLR9 present in endocytic vesicles (Latz, et al. Nature Immunol. (2004) 5:190-198). The resultant immune response is characterized by the production of polyreactive IgM antibodies, cytokines, and chemokines which induce T-helper 1 immunity (Lipford, et al., Eur. J. Immunol. (1997) 27:2340-2344; Weiner, J. Leukocyte Biol. (2000) 68:445-463; Stacey, et al., Curr. Topics Microbiol. Immunol. (2000) 247:41-58; Jacob, et al., J. Immunol. (1998) 161:3042-3049). The TLR9 receptor recognizes CpG ODNs with a strict bias for the chemical and conformational nature of the unmethylated CpG ODN since conjugation of an oligonucleotide and a CpG DNA at the 5'-end has been shown to reduce significantly the immunostimulatory activity of the CpG DNA. On the other hand, conjugation of an oligonucleotide and a CpG ODN at the 3'-end does not perturb or may even enhance the immunostimulatory activity of the CpG DNA (Kandimilla, et al., Bioconjug. Chem. (2002) 13:966-974).

Recently, investigators have established three classes of CpG ODNs: CpG-A, CpG-B, and CpG-C (Verthelyi, et al., J. Immunol. (2001) 166:2372-2377; Krug, et al, Eur. J. Immunol. (2001) 31:2154-2163; Rothenfusser, et al., Blood (2004) 103:2162-2169; Vollmer, et al, Eur. J. Immunol. (2004) 34:252-262). CpG-A ODNs are potent inducers of natural killer cell activation and interferon-α secretion; CpG-B ODNs predominantly elicit B-cell proliferation and plasmacytoid dendritic cells; and CpG-C ODNs have the activity of both CpG-A and CpG-B and therefore induce both NK, plasmacytoid dendritic cell, and B-cell activation. In contrast to the first two classes, CpG-C ODNs are characterized by the absence of poly-G stretches and have palidromic sequences combined with stimulatory CpG motifs (Vollmer, et al, Eur. J. Immunol. (2004) 34:252-262).

CpG ODNs have shown efficacy in mouse models as a monotherapy (Klinman, Nature Rev. Immunol. (2004) 4:249-258; Lonsdorf, et al., J. Immunol. (2003) 171:3941-3946; Ishii et al., Clin. Cancer Res. (2003) 9:6516-6522; Baines and Celis, Clin. Cancer Res. (2003) 9:2693-2700). Direct injection of CpG ODN into tumor lesions is reported to activate local dendritic cells and induces the production of IL-12 in and around the tumor. In several different tumor models, injection of CpG-B ODN led to regression of established tumors in a T-cell dependent fashion. In a B-16 melanoma model, injection of CpG-A ODNs either into the tumor or systemically led to tumor regression in an NK dependent, T-cell independent manner (Lonsdorf, et al., J. Immunol. (2003) 171:3941-3946).

CpG ODNs have shown efficacy in mouse models when administered in combination with antitumor antibodies (Wooldridge et al, Blood (1997) 89:2994-2998). Administration of CpG ODN was found to activate dramatically ADCC effector cells and induce expression of CD64. When this treatment was followed by injection of an antitumor antibody, dramatic increases in biologic activity were seen. Regression was achieved with large tumors that would not normally respond to antibody therapy alone, as well as with tumors that only express the target antigen at low concentrations.

CpG ODNs have also shown efficacy as radiotherapy enhancers. Recent results have shown that CpG ODNs are potent enhancers of tumor radioresponse and as such have potential to improve clinical radiotherapy (Milas, et al., Cancer Res. (2004) 64:5074-5077). Likewise, CpG ODN therapy has been shown to be enhanced by prior chemotherapy and as such have the potential to improve with prior drug therapy (Li and Levy, Abstract, 19th Intl. Soc. Biol. Therapy, San Francisco, (2004).

Further improvements in the design of cancer immunotherapeutic treatments are needed.

SUMMARY OF THE INVENTION

Provided is a cancer therapeutic agent comprising a cancer targeting molecule linked to an oligonucleotide comprising an immunostimulatory sequence motif which contains at least one unmethylated CG dinucleotide. In one embodiment, the oligonucleotide contains multiple such immunostimulatory motifs which may be all the same or a mixture of different motifs. In another embodiment, the immunostimulatory motif of the oligonucleotide contains TCGTT and/or TCGTA with the CG dinucleotide unmethylated.

Also provided is a method of reducing the size of a tumor or inhibiting the growth of cancer cells or reducing or inhibiting the development of metastatic cancer in an individual with cancer, comprising administering an effective amount of a cancer therapeutic agent comprising a cancer targeting molecule linked to a oligonucleotide comprising an immunostimulatory sequence motif which contains at least one unmethylated CG dinucleotide.

In one embodiment, the cancer targeting molecule of the immunoconjugate is an antibody. The antibody can be specific for a tumor cell-surface antigen, a stromal component of a tumor, an intracellular antigen or an intranuclear antigen. In the latter case, the antibody can be a murine, chimeric, humanized, or human form of murine antibody TNT-1, TNT-2, or TNT-3 or is NHS76.

The cancer therapeutic methods described herein may further include administration of an agent that reduces the immunoregulatory T cell activity in the individual. educing immunoregulatory T cell activity is achieved by removing ex vivo immunoregulatory T cells from the individual. Reducing immunoregulatory T cell activity may be achieved by administering an agent to the individual that depletes or inactivates immunoregulatory T cells in the individual.

Reducing immunoregulatory T cell activity also may be achieved using at least one antibody that binds to the immunoregulatory T cells. Such antibody may be selected from the group consisting of anti-CD4, anti-CD25, anti-neuropilin, and anti-CTLA4. Reducing immunoregulatory T cell activity also may be achieved by administering a GITR ligand agonist.

Immunoregulatory T cell activity may be reduced in the individual before, during or after administering the cancer therapeutic agent.

The cancer therapeutic methods described herein may also include administering T cells which have cytotoxic activity against the cancer. This may be achieved by adoptive transfer of immune cells. These immune cells are preferably T cells, which may be activated ex vivo. In one embodiment, activation is achieved by exposure to IL-2 and/or anti-CD3 antibody. In another embodiment, ex vivo activation is achieved by exposure to the cancer cells or to a cancer cell vaccine. Adoptive transfer of immune cells may occur before, during or after administering the invention agent. Adoptive transfer is preferably given after removal, depletion or inactivation of immunoregulatory T cells.

As used herein, an "oligonucleotide comprising an immunostimulatory sequence motif which contains at least one unmethylated CG dinucleotide" includes sequences that bind to the TLR9 receptor on B cells and plasmacytoid dendritic cells (pDCs) and initiate an immunostimulatory response. Such response may include maturation, differentiation and/or proliferation of natural killer (NK) cells, T cells and monocytes/macrophages. Many such immunostimulatory sequence motifs are known and described in the art while others may be identified by routine efforts.

An immunostimulatory sequence motif which contains at least one unmethylated CG dinucleotide refers to the portion of an oligonucleotide that includes the unmethylated CG dinucleotide and several nucleotides on each side of the CpG that are critical for the immunostimulatory activity. For example, the immunostimulatory motif containing the CpG dinucleotide is shown bolded and italicized with the CpG bolded and underlined in the following sequence: 5'-TCGT CGTTT-3'.

Oligonucleotides which comprise an immunostimulatory sequence motif that contains at least one unmethylated CG dinucleotide have been referred to the in art as "oligodeoxynucleotide containing unmethylated CpG motifs," or "CpG oligodeoxynucleotides ("CpG ODNs"). The phrase "oligonucleotide comprising, an immunostimulatory sequence motif which contains at least one unmethylated CG dinucleotide" may be referred to herein as a "CpG immunostimulatory oligonucleotide."

Cells stimulated by CpG immunostimulatory oligonucleotide secrete cytokines and chemokines (IL-1, IL-6, IL-18 and TNF) including Th1-biased cytokines (interferon-γ, IFN-γ, and IL-12) to create a pro-inflammatory immune response (Klinman, Nature Rev. Immunol. (2004) 4:249-258). Also stimulated are professional antigen-presenting cells (APCs) which include macrophages and dendritic cells (Krieg, et al., Nature (1995) 374:546-549; Klinman, et al. PNAS (1996) 93:2879-2883).

The CpG ODN contain one or more unmethylated CG dinucleotides arranged within a specific sequence (Tokunaga, et al., JNCI (1984) 72:955-962; Messina, et al, J. Immunol. (1991) 147:1759-1764; Krieg, et al, Nature (1995) 374:546-549). The optimal CpG flanking region in mice consists of two 5' purines and two 3' pyrimidines, whereas the optimal motif in humans and certain other species is TCGTT and/or TCGTA (Klinman, Nature Rev. Immunol. (2004) 4:249-258). The CpG immunostimulatory oligonucleotide is generally from 6 to 100 nucleotides in length, more preferably between about 15 to 25 nucleotides in length. As described by Sen et al., (Cell Immunol. 2004 November-December; 232(1-2):64-74), portions of an oligonucleotide that has immunostimulatory motifs containing an unmethylated CpG can be replaced with RNA. For example, the RNA can be used in the oligonucleotide to flank the critical immunostimulatory motif.

The TLR9 receptor has been reported to diverge through evolution, so the precise sequence motifs (unmethylated CpG dinucleotides plus flanking regions) optimal for stimulating immune cells from different animal species varies (Klinman, Nature Rev. Immunol. (2004) 4:249-258). For example, the TLR9 molecules in mice differ from those in humans by 24% at the amino-acid level. It has been reported that the cell populations that express TLR9 have been reported to differ between species (Klinman, Nature Rev. Immunol. (2004) 4:249-258). In mice, immune cells of the myeloid lineage (including monocytes, macrophages and myeloid DCs) express TLR9 and respond to CpG stimulation, whereas in humans, these cell types generally do not express TLR9 and cannot be directly activated by CpG ODNs (Klinman, Nature Rev. Immunol. (2004) 4:249-258). The structural characteristics of human TLR9 are found in the Swiss-Prot database under accession no. Q9NR96. The molecule is synthesized as a 1032 amino acid precursor of which about 25 amino acids are removed as a leader sequence leaving a 1007 amino acid receptor.

DETAILED DESCRIPTION OF THE INVENTION

Figure 1:
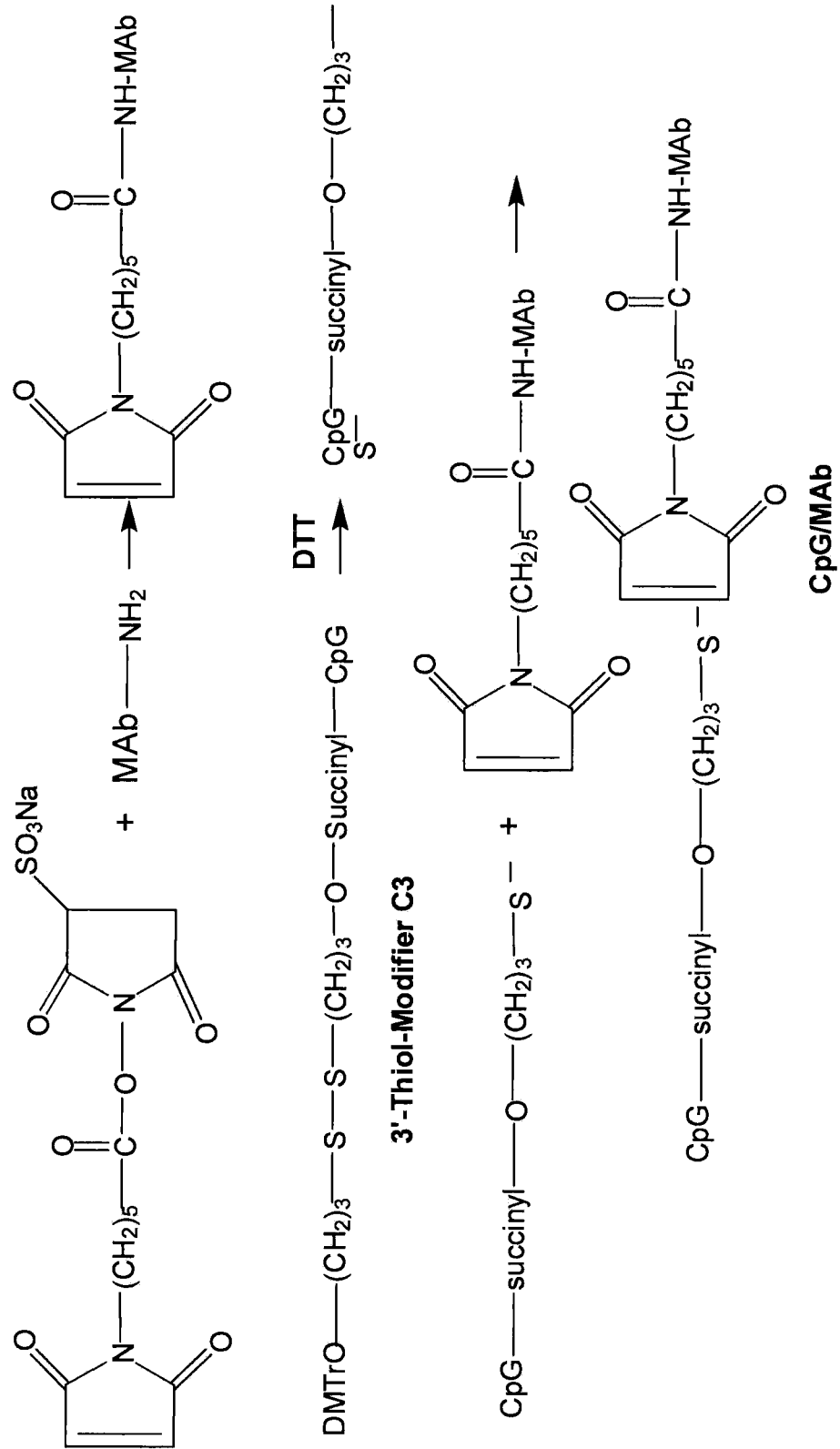
FIG. 1 discloses a scheme for preparing a CpG ODN antibody conjugate by crosslinking with EMCS.

Cancer therapeutic agents are described that comprise a tumor targeting agent linked to an oligonucleotide comprising an immunostimulatory sequence motif which contains at least one unmethylated CG dinucleotide. Linkage can be achieved by any of a variety of approaches provided that the tumor targeting agent retains its ability to bind to its cognate antigen and the oligonucleotide comprising an immunostimulatory sequence motif which contains at least one unmethylated CG dinucleotide retains its immune stimulatory activity. Initial activity testing can be done in vitro and followed by pharmacokinetic, biodistribution and radioimmunoscintigraphy analysis conducted in tumor-bearing animals.

The cancer targeting agent may be linked to multiple immunostimulatory oligonucleotides. For example, a cancer targeting agent may be linked to multiple immunostimulatory oligonucleotides all of which are the same. Alternatively, the a cancer targeting agent may be linked to different immunostimulatory oligonucleotides.

As used herein, "cancer therapeutic agent" refers to a conjugate formed between a cancer targeting molecule and an oligonucleotide comprising an immunostimulatory sequence motif which contains at least one unmethylated CG dinucleotide. A preferred cancer targeting molecule is an antibody. An antibody containing cancer therapeutic agent can be referred to as an immunoconjugate.

As used herein, "linked" means that under physiological conditions of pH, ionic strength and osmotic potential, the majority of the entities are associated with each other at equilibrium. Covalent linkage may be by any of a variety of chemical linking and crosslinking agents including, for example, homobifunctional or heterobifunctional crosslinking reagents, many of which are commercially available (see, e.g., Pierce Chemical Co. or Sigma Chemical Co.). Linking or crosslinking can be achieved by any of a variety of chemistries well known in the art including, for example, activated polyethylene glycols, aldehydes, isocyanates, maleimides and the like.

Oligonucleotides comprising an immunostimulatory sequence motif which contains at least one unmethylated CG dinucleotide and have in vivo immunostimulatory activity may be used to prepare invention conjugates. In some embodiments, the oligonucleotide may be chemically modified to enable linkage to the cancer targeting molecule. Modification may involve adding a thiol group to the 3' terminal nucleotide using a non-nucleoside linker (3'-thiol-modifier C3) (Zukermann et al., Nucleic Acids Res, 15: 5305-5321, 1987) to facilitate covalent linkage with linker modified antibody. The following CpG immunostimulatory oligonucleotides are exemplary (CpG motifs identified by bolded text with underlining).

```
SEQ ID NO: 1 (CpG-1826):
5'-TCCATGACGTTCCTGACGTT-3' (class A)

SEQ ID NO: 2: (untitled):
5'-TCTCCCAGCGTGCGCCAT-3' (class A)

SEQ ID NO: 3 (CpG-2395):
```

-continued

```
5'-TCGTCGTTTTCGGCGCGCGCCG (class C)

SEQ ID NO: 4 (CpG-1668):
5'-TCCATGACGTTCCTGATGCT-3'
```

CpG immunostimulatory oligonucleotides for human application:

```
SEQ ID NO: 5 (CpG-2006):
5'-TCGTCGTTTTGTCGTTTTGTCGTT (class B)

SEQ ID NO: 6 (CpG 1585):
5' GGGGTCAACGTTGAGGGGGG 3'

SEQ ID NO: 7 (CpG 2216):
5' GGGGGACGATCGTCGGGGGG 3'

SEQ ID NO: 8 (CpG 2395):
5' TCGTCGTTTTCGGCGCGCGCCG 3'

SEQ ID NO: 9 (CpG 5397):
5' TCGTCGTTTTCCGGCGCGCCGG 3'

SEQ ID NO: 10 (CpG 2429):
5' TCGTCGTTTTCGGCGGCCGCCG 3'

SEQ ID NO: 11 (K23):
5' TCGAGCGTTCTC 3'

SEQ ID NO: 12 (D35):
5' GGTGCATCGATGCAGGGGGG 3'

SEQ ID NO: 13 (CpG 2059):
5' TCGTCGTTTTGTCGTTTTCTCGT 3'
```

CpG immunostimulatory oligonucleotides having applications for human use include class A, B or C type CpG ODNs which are well known and may linked to a cancer targeting molecule as described herein. Exemplary such CpG immunostimulatory oligonucleotides are described in the following:

CpG 7909 for lymphoma therapy
Wooldridge, J, Link, B K, Weisdorf, D J, et al. Phase I study of oligodeoxynucleotide CpG 7909 in patients with previously treated non-Hodgkin's lymphoma. ASCO 2003; abstract 843.

CpG 2080
Hartmann, G. and Krieg, A M. Mechanism and function of a newly identified CpG DNA motif in human primary B cells. J. Immunol. 164:944-952, 2000.

K23 and D-35 ODN
Gursel, M, Verthelyi, D, Gursel, I, Ishii, K, and Klinman, D M. Differential and completive activation of human immune cells by distinct classes of CpG oligodeoxynucleotide. J. Leukocyte Biology 71:813-820, 2002.

Human Toll-like receptor 9 is optimally triggered by the motif GTCGTT Bauer, S. et al. Human TLR9 confers responsiveness to bacterial DNA via species-specific CpG motif recognition. PNAS 98:9237-9242, 2001.

Hartmann et al. Delineation of a CpG phosphorothioate oligodeoxynucleotide for activating primate immune responses in vitro and in vivo. J. Immunology 164: 1617-1624, 2000.

K3, K19, K110 and others (sequences shown)
Leifer, C A, Daniela, V, and Klinman, D M. Heterogeneity in the human response to immunostimulatory CpG Oligodeoxynucleotides. J. Immunotherapy 26:313-319, 2003.

CpG 2006 and C-2395
Vollmer et al. Characterization of three CpG oligodeoxy-nucleotide classes with distinct immunostimulatory activities. Eur. J. Immunol. 34:251-262, 2004.

CpG 2006
Gantner, F, Hermann, P, Nakashima, K, Matsukawa, S, Sakai, K, and Bacon, KB>CD40-dependent and -independent activation of human tonsil B cells by CpG oligodeoxynucleotides. Eur. J. Immunology 33:1576-1585, 2003.

CpG-A type (CpG 2216, CpG 1585); CpG-B (CpG 2006)
Rothenfusser, et al. CpG-A and CpG-B oligonucleotides differentially enhance human peptide-specific primary and memory CD8+ T-cell responses in vitro. Blood 103:2162-2169, 2004.

An exemplary CpG immunostimulatory oligonucleotide class A is CpG-1826 (Ballas et al., J. Immunol. 167: 4878-86, 2001), which has two motifs (5'-GACGTT-3') and has been shown to induce immunostimulatory activity in mice (Baines et al., Clin. Cancer Res. (2003) 9:2693-2700; Lonsdorf et al. J. Immunol. (2003) 171:3941-3946). A 20-mer CpG ODN (SEQ ID NO: 2) is also useful because it has a significant effect on murine NK cells with little effect on murine B cells (Wooldridge et al., Blood (1997) 89:2994-2998). Other CpG ODN have been reported in the literature and can be used to link to an antibody (Krieg et al., Nature (1995) 374:546-549; Bauer et al., J. Immunol. (2001) 166: 5000-5007).

SEQ ID NO: 3 has been described to be active on murine B-cells by Gursel et al. (J. Leukocyte Biol. (71:813-820), while a class C CpG motif, SEQ ID NO:4 (CpG-2395) was described by Vollmer et al. (Eur. J. Immunol. (2004) 34:252-262).

Particular oligonucleotides including the GpC type may be used as a negative control in experimental analysis of CpG immunostimulatory oligonucleotide and invention conjugates.

```
SEQ ID NO: 14 (1745):
5'-TCCAATGAGCTTCCTGAGTCT-3' (negative control)

SEQ ID NO: 15 (GpC-1982):
5'-TCCAGGACTTCTCTCAGGTT-3' (negative control)

SEQ ID NO: 16 (GpC-1668):
5'-TCCATGAGGTTCCTGATGCT-3' (negative control)
```

SEQ ID NO: 6, (CpG-1745) has been previously shown to have no CpG immunostimulatory activity.

CpG immunostimulatory oligonucleotides (or control sequences) may be synthesized by replacing the phosphodiester backbone with a phosphorothioate linkage ("PS linkage"). PS forms of CpG immunostimulatory oligonucleotides display an extremely high degree of nuclease resistance and stability (Stein et al. Nucleic Acids Res. (1988) 16:3209-3221). CpG immunostimulatory oligonucleotides also may be used in which part has the phosphodiester backbone and part has an alternative backbone such as a phosphorothioate linkage. CpG immunostimulatory oligonucleotide sequences not disclosed herein may be prepared along principles of those currently known. CpG immunostimulatory oligonucleotides may be prepared with different backbone chemistry provided that the resulting CpG immunostimulatory oligonucleotides can stimulate the immune response as described herein.

For quality assurance, endotoxin levels of all oligonucleotides, antibodies and the invention conjugates can be measured by *Limulus amebocyte* lysate assay (Bio-Whitaker, Walkersville, Md.) to confirm that levels are below 0.01 Units/ml.

As used herein, "cancer targeting molecule" refers to a molecule that has the ability to localize to cancer cells in an individual. The phrase "localizing to cancer cells in an individual" (i.e., "in vivo") means that the agent can bind to a tumor cell(s) or can bind in the vicinity of a tumor cell(s) following administration to the individual. The cancer targeting molecule may bind to a receptor or ligand on the surface of the cancer cell or may bind to an intracellular target of cancer cell provided that the target is accessible to the molecule. Accessibility to intracellular cancer cell targets may arise in cancer cells that have a compromised plasma membrane such as cells which are undergoing apoptosis, necrosis, and the like. Some cancer targeting molecules can bind intracellular portions of a cell that does not have a compromised plasma membrane. See e.g., Porkka et al., Proc Natl Acad Sci USA. (2002) 99(11): 7444-9.

Cancer targeting molecules also may bind to a target that is present in the tumor. As used herein "tumor" includes cancer cells, necrosis, as well as stroma. Stroma includes cells such as fibroblasts and endothelial cells of vessels and capillaries and extracellular matrix, which is composed of fibrillar and non-fibrillar components. The major fibrillar proteins are collagen and elastin. A cancer targeting molecule may target to the tumor by binding to the stroma which surrounds the cancer cells in the tumor. Thus, a cancer targeting molecule may target in the vicinity of a cancer by binding to a stromal component such as a fibroblast or endothelial cell or a component of the extracellular matrix. See, e.g. Schraa et al. Control Release (2002) 83(2): 241-51; Arap et al. Haemostasis (2001) 31 Suppl 1: 30-1.

Cancer targeting molecules useful in the present invention include those that bind to tumor specific or tumor associated antigens. The term "tumor associated antigen" (TAA) as used herein refers to a protein which is present on tumor cells, and on normal cells during fetal life (onco-fetal antigens), after birth in selected organs, or on normal cells, but at much lower concentration than on tumor cells. A TAA also may be present in the stroma in the vicinity of the cancer cell but be expressed at lower amounts in the stroma elsewhere in the body. A variety of TAA have been described including BRCA-1 and BRCA-2 proteins, the HER-2-neu, mucins such as MUC1, integrins, cytokines, and the like. In contrast, tumor specific antigen (TSA) (aka. "tumor-specific transplantation antigen" or TSTA) refers to a tumor cell expressed molecule absent from normal cells. TSA usually appear when an infecting virus has caused the cell to become immortal and express viral antigens. Exemplary viral TSAs are the E6 or E7 proteins of HPV type 16. TSAs not induced by viruses can be idiotypes of the immunoglobulin on B cell lymphomas or the T cell receptor (TCR) on T cell lymphomas.

Cancers treatable using the methods of the invention include carcinomas, sarcomas, and leukemias and lymphomas and other types of cancer. Carcinomas include those of lung, breast, colon, ovarian, prostate, and the like. These cancers may be primary or metastatic. In the case of leukemias and lymphomas, the cancer cells treatable with the invention methods include those in the form of a tumor as well as cancer cells in the bone marrow and in the circulation.

Cancer targeting molecules include small molecule compounds such as drugs, organic compounds, peptides, peptidomimetics, as well as larger molecules such as glycoproteins, proteoglycans, lipids glycolipids, phospholipids, lipopolysaccharide, nucleic acids, proteoglycans, carbohydrates, and the like. Small molecule cancer targeting molecules may be about 5,000 daltons or less in size. Cancer targeting molecules may include well known therapeutic compounds including anti-neoplastic agents. Anti-neoplastic targeting molecules may include paclitaxel, daunorubicin, doxorubicin, caminomycin, 4'-epiadriamycin, 4-demethoxy-daunomycin, 11-deoxydaunorubicin, 13-deoxydaunorubicin, adriamycin-14-benzoate, adriamycin-14-octanoate, adriamycin-14-naphthaleneacetate, vinblastine, vincristine, mitomycin C, N-methyl mitomycin C, bleomycin A2, dideazatetrahydrofolic acid, aminopterin, methotrexate, cholchicine and cisplatin, and the like. Cancer targeting molecules also may include toxins such as diphtheria toxin, cytokines such as CSF, GSF, GMCSF, TNF, erythropoietin, immunomodulators or cytokines such as the interferons or interleukins, a neuropeptide, reproductive hormone such as HGH, FSH, or LH, thyroid hormone, neurotransmitters such as acetylcholine, and hormone receptors such as the estrogen receptor.

Cancer targeting molecules can be a protein or peptide. "Polypeptide", "peptide," and "protein" are used interchangeably to refer to a polymer of amino acid residues linked by amide bonds. As used herein, these terms apply to amino acid polymers in which one or more amino acid residue is an artificial chemical analogue of a corresponding naturally occurring amino acid. Thus, proteins may include natural and non-natural amino acids. Amino acids can be in the L or D form as long as the binding function of the peptide is maintained. Peptides can be of variable length, but are generally between about 4 and 200 amino acids in length. Peptides may be cyclic, having an intramolecular bond between two non-adjacent amino acids within the peptide, e.g., backbone to backbone, side-chain to backbone and side-chain to side-chain cyclization. Cyclic peptides can be prepared by methods well know in the art. See e.g., U.S. Pat. No. 6,013,625.

The cancer targeting molecule may be an antagonist or agonist of an integrin. Integrin is a heterodimeric transmembrane glycoprotein complex that functions in cellular adhesion events and signal transduction processes. Integrins, which comprise and alpha and a beta subunit, include numerous types including $\alpha_1\beta_1$, $\alpha_2\beta_1$, $\alpha_3\beta_1$, $\alpha_4\beta_1$, $\alpha_5\beta_1$, $\alpha_6\beta_1$, $\alpha_7\beta_1$, $\alpha_8\beta_1$, $\alpha_9\beta_1$, $\alpha_1\beta_1$, $\alpha_6\beta_4$, $\alpha_4\beta_7$, $\alpha_D\beta_2$, $\alpha_D\beta_2$, $\alpha_L\beta_2$, $\alpha_M\beta_2$, $\alpha_v\beta_1$, $\alpha_v\beta_3$, $\alpha_v\beta_5$, $\alpha_v\beta_6$, $\alpha_v\beta_8$, $\alpha_x\beta_2$, $\alpha_{11b}\beta_3$, $\alpha_{1ELb}\beta_7$, and the like. Integrin $\alpha_v\beta_3$ is expressed on a variety of cells and has been shown to mediate several biologically relevant processes, including adhesion of osteoclasts to bone matrix, migration of vascular smooth muscle cells, and angiogenesis. Suitable targeting molecules for integrins include RGD peptides or peptidomimetics or non-RGD peptides or peptidomimetics (see, e.g., U.S. Pat. Nos. 5,767,071 and 5,780,426) as well as for other integrins such as $\alpha_4\beta_1$(VLA-4), $\alpha_4\beta_7$ (see, e.g., U.S. Pat. No. 6,365,619; Chang et al., Bioorganic & Medicinal Chem Lett, 12:159-163 (2002); Lin et al., Bioorganic & Medicinal Chem Lett, 12:133-136 (2002)), and the like.

A preferred cancer targeting molecule is an antibody. The term "antibody" as used herein includes immunoglobulins, which are the product of B cells and variants thereof as well as the T cell receptor (TCR), which is the product of T cells, and variants thereof. An immunoglobulin is a protein comprising one or more polypeptides substantially encoded by the immunoglobulin kappa and lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Also subclasses of the heavy chain are known. For example, IgG heavy chains in humans can be any of IgG1, IgG2, IgG3 and IgG4 subclass.

A typical immunoglobulin structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain (VL) and variable heavy chain (VH) refer to these light and heavy chains respectively.

Antibodies exist as full length intact antibodies or as a number of well-characterized fragments produced by digestion with various peptidases or chemicals. Thus, for example, pepsin digests an antibody below the disulfide linkages in the hinge region to produce F(ab')2, a dimer of Fab, which itself is a light chain joined to VH—CH1 by a disulfide bond. The F(ab')2 may be reduced under mild conditions to break the disulfide linkage in the hinge region thereby converting the F(ab')2 dimer into an Fab' monomer. The Fab' monomer is essentially a Fab fragment with part of the hinge region (see, Fundamental Immunology, W. E. Paul, ed., Raven Press, N.Y. (1993), for a more detailed description of other antibody fragments). A Fab fragment and Fc fragment are generated by digesting IgG with papain. Papain cleaves in the hinge region just above the residues involved in interchain S—S bonding, resulting in monovalent Fab fragments and the Fc fragment, which includes two constant region fragments, each containing the lower part of the hinge, CH2 and CH3 domains. The constant region fragments of the Fc are stabilized as a dimer though interchain S—S bonding of the lower residues of the hinge region.

Immunoglobulin "Fc" classically refers to the portion of the constant region generated by digestion with papain. Includes the lower hinge which has the interchain S—S bonds. The term "Fc" as used herein refers to a dimeric protein comprising a pair of immunoglobulin constant region polypeptides, each containing the lower part of the hinge, CH2 and CH3 domain. Such "Fc" fragment may or may not contain S—S interchain bridging in the hinge region. It should be understood that an Fc may be from any Ig class and, as such, may include a CH4 domain such as in the case of IgM. Mutant sequences of an Fc are known such as described by Wines et al., J Immunol. 2000 May 15; 164(10):5313-8 and may be used herein.

While various antibody fragments are defined in terms of the digestion of an intact antibody, one of skill will appreciate that any of a variety of antibody fragments may be synthesized de novo either chemically or by utilizing recombinant DNA methodology. Thus, the term antibody, as used herein also includes antibody fragments either produced by the modification of whole antibodies or synthesized de novo or antibodies and fragments obtained by using recombinant DNA methodologies.

Recombinant antibodies may be conventional full length antibodies, antibody fragments known from proteolytic digestion, unique antibody fragments such as Fv or single chain Fv (scFv), domain deleted antibodies, and the like. Fragments may include a domains or polypeptides with as little as one or a few amino acid deleted or mutated while more extensive deletion is possible such as deletion of one or more domains.

An Fv antibody is about 50 Kd in size and comprises the variable regions of the light and heavy chain. A single chain Fv ("scFv") polypeptide is a covalently linked VH::VL heterodimer which may be expressed from a nucleic acid including VH- and VL-encoding sequences either joined directly or joined by a peptide-encoding linker. See Huston, et al. (1988) Proc. Nat. Acad. Sci. USA, 85:5879-5883. A number of structures for converting the naturally aggregated, but chemically separated light and heavy polypeptide chains from an antibody V region into an scFv molecule which will fold into a three dimensional structure substantially similar to the structure of an antigen-binding site. See, e.g. U.S. Pat. Nos. 5,091,513, 5,132,405 and 4,956,778.

An antibody may be a non-human antibody, a human antibody, a humanized antibody or a chimeric antibody, the latter comprising human and non-human antibody sequence. As is known in the art, chimeric antibody is prepared by exchanging a non-human constant region (heavy chain, light chain or both) with a human constant region antibody. See e.g. U.S. Pat. No. 4,816,567 to Cabilly et al. Methods of making humanized antibodies from non-human antibodies such as from murine antibodies are also well known (see, e.g., U.S. Pat. No. 5,565,332 to Winter).

A cancer targeting molecule may be an antibody that targets to a nuclear antigen that is accessible in necrotic portions of a tumor. Necrotic cell targeting also known as Tumor Necrosis Therapy (TNT) (Epstein et al. (Cancer Res. (1988) 48:5842-5848; Chen et al., Cancer Res. (1989) 49:4578-4585; Hornick et al., Cancer Biotherapy and Radiopharmaceuticals (1998) 13:255-268; Sharifi et al., Hybridoma and Hybridomics (2001) 20:305-312) represents a different approach from methods that employ antibodies that bind to tumor-associated cell surface antigens and require the use of different antibodies for each type of tumor. TNT antibodies bind intracellular antigens found in all cells and which are retained by dying cells and which show preferential localization in malignant tumors due to the presence of abnormally permeable, degenerating cells only rarely present in normal tissues. Rapidly dividing tumors contain a proportion of degenerating or dead cells, but, with attention focused upon attempts to kill the dividing cells, the degenerating component has largely been ignored. Calculations of tumor cell loss have revealed that, in contrast to normal tissues, 30-80% of the progeny of tumor cell divisions shortly undergo degeneration. In tumors, the imperfect vasculature and impaired phagocytic response, permit the accumulation of degenerating cells, often with the formation of large areas of necrosis, long recognized by pathologists to be a typical feature of malignant tumors (Epstein, et al., Cancer Res (1988) 48:5842-5848). Thus, the accumulation within tumors of a high proportion of dying cells constitutes a major distinction between malignant tumors and normal tissues wherein sporadic cell death occurs at a relatively low rate and is accompanied by a rapid (within minutes) and orderly removal of necrotic elements from the tissue. Since degenerating cells have a permeable cell surface membrane not observed in viable cells, TNT antibodies enter and bind to their intracellular antigens in necrotic areas of the tumor. Contrarily, TNT antibodies diffusing in viable regions of the tumor and normal tissues do not bind and are removed from the circulation by normal clearance mechanisms. Hence, TNT antibodies provide a useful approach for specifically targeting necrotic regions of tumors and can be used to deliver diagnostic and therapeutic reagents into these regions which are may be situated deep within the central core of tumors. TNT antibodies have a number of unique features that distinguishes from other forms of antibody therapy. Because of these attributes, TNT antibodies have several advantages that enable the delivery of radionuclides (Epstein et al. (Cancer Res. (1988) 48:5842-5848; Hornick et al., Cancer Biotherapy and Radiopharmaceuticals (1998) 13:255-268), immunostimulatory molecules (Li et al., J. Immunother. (2003) 26:320-331; Li et al., Cancer Res. (2003) 63:8384-8392)), and vasopermeability agents (LeBerthon et al., Cancer Res. (1991) 51:2694-2698; Khawli et al, Cancer (1994) 73:824-831; Hornick et al., Clin Cancer Res. (1999) 5:51-60) for the treatment of cancer.

In one embodiment, the cancer targeting antibody is specific for a tumor cell-surface antigen. In another embodiment, the antibody is specific for a stromal component of a tumor. In yet another embodiment, the antibody is specific for an intracellular antigen, such as an intranuclear antigen (s). In the latter case, the antibody may be a humanized or human chimeric antibody based on the murine antibody TNT-1, TNT-2, TNT-3. The human antibody NHS76 is a genetically engineered counterpart to TNT-1. The sequence of TNT antibody NHS76 can be found in U.S. Pat. No. 6,827,925.

Homology or identity is often measured using sequence analysis software (e.g., Sequence Analysis Software Package of the Genetics Computer Group, University of Wisconsin Biotechnology Center, 1710 University Avenue, Madison, Wis. 53705). Such software matches similar sequences by assigning degrees of homology to various deletions, substitutions and other modifications. The terms "homology" and "identity" in the context of two or more nucleic acids or polypeptide sequences, refer to two or more sequences or subsequences that are the same or have a specified percentage of amino acid residues or nucleotides that are the same when compared and aligned for maximum correspondence over a comparison window or designated region as measured using any number of sequence comparison algorithms or by manual alignment and visual inspection For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

Methods of alignment of sequence for comparison are well-known in the art. Optimal alignment of sequences for comparison can be conducted, e.g., by the local homology algorithm of Smith and Waterman (1981, Adv. Appl. Math. 2:482) by the homology alignment algorithm of Needleman and Wunsch, (1970, J. Mol. Biol. 48:443) by the search for similarity method of Person and Lipman (1988, Proc. Nat'l. Acad. Sci. USA 85:2444) by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection. Other algorithms for determining homology or identity include, for example, in addition to a BLAST program (Basic Local Alignment Search Tool at the National Center for Biological Information), ALIGN, AMAS (Analysis of Multiply Aligned Sequences), AMPS (Protein Multiple Sequence Alignment), ASSET (Aligned Segment Statistical Evaluation Tool), BANDS, BESTSCOR, BIOSCAN (Biological Sequence Comparative Analysis Node), BLIMPS (BLocks IMProved Searcher), FASTA, Intervals & Points, BMB, CLUSTAL V, CLUSTAL W, CONSENSUS, LCONSENSUS, WCONSENSUS, Smith-Waterman algorithm, DARWIN, Las Vegas algorithm, FNAT (Forced Nucleotide Alignment Tool), Framealign, Framesearch, DYNAMIC, FILTER, FSAP (Fristensky Sequence Analysis Package), GAP (Global Alignment Program), GENAL, GIBBS, GenQuest, ISSC (Sensitive Sequence Comparison), LALIGN (Local Sequence Alignment), LCP (Local Content Program), MACAW (Multiple Alignment Construction & Analysis Workbench), MAP (Multiple Alignment Program), MBLKP, MBLKN, PIMA (Pattern-Induced Multi-sequence Alignment), SAGA (Sequence Alignment by Genetic Algorithm) and WHAT-IF. Such alignment programs can also be used to screen genome databases to identify polynucleotide sequences having substantially identical sequences. For example, a substantial portion of the human genome sequence is available for searching via the BLAST search tool at the National Center for Biotechnology Information (NCBI). Information about multiple sequenced genomes and the resources to analyze them also is available from NCBI on its Genomic Biology web page.

One example of a useful algorithm is BLAST (e.g., BLAST 2.0), which is described in Altschul et al., 1977, Nucl. Acids Res. 25:3389-3402, and Altschul et al., J. Mol. Biol., 1990 215:403-410, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra, 1977 and 1990). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment.

The BLASTN program (for nucleotide sequences) uses as defaults a word length (W) of 11, an expectation (E) of 10, M=5, N=−4 and a comparison of both strands. For amino acid sequences, the BLASTP program uses as defaults a word length of 3, and expectations (E) of 10, and the BLOSUM62 scoring matrix (see Henikoff and Henikoff, Proc. Natl. Acad. Sci. USA (1989) 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul, 1993, Proc. Natl. Acad. Sci. USA 90:5873). One measure of similarity provided by BLAST algorithm is the smallest sum probability (P(N)), which provides an indication of the probability by which a match between two nucleotide or amino acid sequences would occur by chance. For example, a nucleic acid is considered similar to a references sequence if the smallest sum probability in a comparison of the test nucleic acid to the reference nucleic acid is less than about 0.2, more preferably less than about 0.01, and most preferably less than about 0.001.

Antibodies may be prepared using recombinant expression methods such as in prokaryotic or eukaryotic cells as is well known in the art. (see e.g., U.S. Pat. Nos. 5,116,943 and 6,331,415). In general, nucleic acid encoding the protein can be cloned into an expression vector for high yield expression of the encoded product. The expression vector can be part of a plasmid, virus, or may be a nucleic acid fragment. The expression vector includes an expression cassette into which the nucleic acid encoding the protein is cloned in operable association with a promoter and optionally an enhancer. The expression cassette may also include other features such as an origin of replication, and/or chromosome integration elements such as retroviral LTRs, or adeno associated viral (AAV) ITRs. If secretion of the protein is desired, DNA encoding a signal sequence may be placed upstream of the nucleic acid encoding the mature amino acids of the protein. DNA encoding a short protein sequence that could be used to facilitate later purification (e.g., a histidine tag) or assist in labeling the protein may be included within or at the ends of the protein encoding nucleic acid.

Cells suitable for replicating and for supporting recombinant expression of protein are well known in the art. Such cells may be transfected or transduced as appropriate with the particular expression vector and large quantities of vector containing cells can be grown for seeding large scale fermenters to obtain sufficient quantities of the protein for clinical applications. Such cells may include prokaryotic microorganisms, such as *E. coli*, or various other eukaryotic cells, such as Chinese hamster ovary cells (CHO), insect cells, or the like. Standard technologies are known in the art to express foreign genes in these systems.

Antibody may be linked to CpG immunostimulatory oligonucleotides using crosslinkers such as maleimide crosslinkers (Table 1), which possess two different reactive groups that allow for conjugations with specific sites on antibodies, minimizing undesirable polymerization or self-conjugation. Sulfo-EMCS (aliphatic maleimide linker) and sulfo-SMPB (aromatic maleimide linker) heterobifunctional crosslinkers (see Table 1 below and associated structures) (Myers et al., J. Immunol. Methods (1989) 121:129-142) are preferred.

TABLE 1

Maleimide Heterobifunctional Crosslinking Reagents

Chemical Name

| | |
|---|---|
| SMCC/Sulfo-SMCC | Sulfosuccinimidyl 4-[N-maleimidomethyl]cyclohexane-1-carboxylate |
| EMCS/Sulfo-EMCS | N-[ε-Maleimidocaproyloxy]sulfosuccinimide ester |
| Sulfo-MBS | m-Maleimidobenzoyl-N-hydroxysulfosuccinimide ester |
| Sulfo-KMUS | N-[κ-Maleimidoundecanoyloxy]sulfosuccinimide ester |
| BMPH | N-[β-Maleimidopropionic acid]Hydrazide•TFA |
| BMPS | N-[β-Maleimidopropyloxy]succinimide ester |
| GMBS/Sulfo-GMBS | N-[γ-Maleimidobutyryloxy]sulfosuccinimide ester |
| SMPB/Sulfo-SMPB | Sulfosuccinimidyl 4-[p-maleimidophenyl]butyrate |
| SMPH | Succinimidyl 4-[p-maleimidophenyl]butyrate |

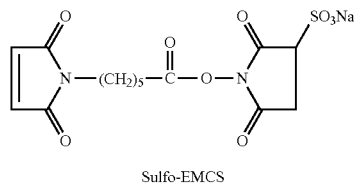

Sulfo-EMCS

TABLE 1-continued

Maleimide Heterobifunctional Crosslinking Reagents

Chemical Name

Sulfo-SMPB

Typically, maleimide crosslinkers are water-soluble analogues and consist of an N-hydroxysuccinimide (NHS) ester and a maleimide group connected with a spacer arm which limits steric hindrance. NHS esters will react with primary amines of the antibody and after purification, the maleimide group will react with the thio functional group of CpG immunostimulatory oligonucleotides (see FIG. 1). The antibody conjugated with the various crosslinkers to CpG immunostimulatory oligonucleotides will be compared for differences in yields, binding of the antibody moiety, and CpG immunostimulatory oligonucleotide activity.

Antibody can be crosslinked according to the standard procedures (e.g., chemical manufacturer's instructions) such as optimized procedures previously described (Khawli et al. Cancer Biother & Radiopharm. (1996) 11:203-215; Sharifi et al., Q. J. Nucl. Med. (1998) 42:242-249). Briefly, antibody is derivatized with conjugation buffer (0.05M PBS, 3 mM EDTA, pH 7.5) for 30 min at room temperature with different molar ratios of the maleimide crosslinking agent to antibody using water-soluble analogues. Excess crosslinking reagents is removed by Sephadex G-25 column chromatography. To a solution of 3'-thiol-modified CpG immunostimulatory oligonucleotide, 0.1M dithiothreitol (DTT/pH 8.3-8.5) is added for 30 min at room temperature (38). Excess DTT is removed by desalting on a Sephadex G-10 column equilibrated with the conjugation buffer as above. Immediately following purification, derivatized antibody is reacted with different molar ratios of 3'-thiol CpG immunostimulatory oligonucleotide to antibody for 1-2 h at room temperature. Free CpG immunostimulatory oligonucleotide is separated from conjugated CpG immunostimulatory oligonucleotide by Sephadex G-50 column chromatography. The different fractions are concentrated, filtered, and further analyzed by sodium dodecylsulfate-polyacrylamide gel electrophoresis (SDS-PAGE) and by high-pressure liquid chromatography (HPLC) to determine purity.

The number of CpG immunostimulatory oligonucleotide molecules per antibody in the conjugate may be determined spectrophotometrically and calculated as $OD_{260}/OD_{280}$ ratio as described by Ngo and Oliva (protocol according to TriLink BioTechnologies, La Jolla, Calif.).

Although the above describes linkage of CpG immunostimulatory oligonucleotide to an antibody, it should be understood that this procedure is merely exemplary and can be applied to link CpG immunostimulatory oligonucleotides to any protein containing cancer targeting molecules.

One may choose linker chemistry that will facilitate release of CpG immunostimulatory oligonucleotides from the invention conjugate within the tumor. This would be useful because CpG immunostimulatory oligonucleotides can enter the cell and bind to the Toll-like receptor 9 (Hemmi et al., Nature (2000) 208:740-745; Tauszig et al., Proc. Natl. Acad. Sci. (USA) (2000) 97:10520-10525). Tumors with significant necrosis may contain abundant enzymes capable of releasing the CpG immunostimulatory oligonucleotides from the invention conjugate for many different linker chemistries. Labile linkers also may be suitable in this regard. For example, an acid-labile heterobifunctional linker that would take advantage of the lower pH of necrotic and hypoxic regions of tumors where lactic acid buildup has been observed (Cooper, Cell Tissue Kinet. (1973) 6:87-95) is advantageous. For example, a maleimide derivative of 2-methylmaleic anhydride (Pierce Chemical) may be used to generate a CpG immunostimulatory oligonucleotide/protein immunoconjugate with an acid-labile bond (Blattner et al., Biochem. (1985) 24:1517-1525; Yang and Reisfeld, Proc. Natl. Acad. Sci. (USA) (1988) 85:1189-1193; Wong, in Chemistry of Protein Conjugation and Crosslinking, Wong SS ED., CRC Press, Fl., 1993, pp 267-293). The reaction of the amino group of the antibody with 2-methylmaleic anhydride gives a substituted maleyl derivative with a carboxamide bond that is stable at or above neutral pH. The derivative can then be coupled to 3'-thio CpG immunostimulatory oligonucleotide. The resulting CpG immunostimulatory oligonucleotide/protein immunoconjugate has a carboxamide bond that is susceptible to hydrolysis under mildly acidic conditions likely to be encountered in the tumor parenchyma, which conditions will foster release of the CpG immunostimulatory oligonucleotide moiety from the targeting agent protein.

Invention conjugates may be evaluated for reactivity and avidity. For example, purified CpG immunostimulatory oligonucleotide/antibody preparations can be radiolabeled with 1-125 using a modified chloramine-T method as described previously (Hornick et al., Cancer Biother. & Radiopharm. (1998) 13:255-268). The in vitro immunoreactivities of radiolabeled fusion proteins can be evaluated by a conventional fixed Raji cell radioimmunoassay (Miller et al., Hybridoma (1993) 12:689-698). Briefly, Raji lymphoma cells are resuspended in freshly prepared 2% paraformaldehyde in PBS to fix the cells and cause disruption of the cell membrane. Radioiodinated preparations (approximately 100,000 cpm/tube) are incubated in triplicate with $10^6$ fixed Raji cells for 1 h. Following incubation, the cells are washed 3 times with 1% bovine serum albumin in PBS. Bound immunoconjugate is detected by measuring the cell pellet-associated radioactivity in a gamma counter.

The avidity constants of invention conjugates may be determined using the methods well known in the art. For example, the method of Frankel and Gerhard (Frankel and Gerhard, Mol. Immunol. (1979) 16:101-106) may be used in which fixed Raji lymphoma cells are incubated in triplicate with increasing amounts of $^{125}$I-labeled conjugate for 1 h with constant mixing. The cells are then washed and the radioactivity measured in a gamma counter. The amount of protein bound is determined by the remaining cell-bound radioactivity (cpm) in each tube and the specific activity (cpm/ng) of the radiolabeled protein is determined from this information. Scatchard plot analysis can be performed to obtain the slope and the equilibrium or avidity constant $K_a$ which will be calculated by the equation K=−(slope/n), where n is the valence of the antibody.

In vitro serum stability of invention conjugates can be evaluated using well known methods such as described previously (Hornick et al., Cancer Biother. & Radiopharm. (1998) 13:225-268). For example, radioiodinated preparations are incubated for 48 h in mouse and/or human serum at 37° C. After trichloroacetic acid precipitation and centrifugation, protein-bound radioactivity is measured in a gamma counter in order to calculate the percentage of intact fusion protein. In addition, the in vitro reactivities of radiolabeled invention conjugates before and after incubation in serum can be determined as described above.

In vitro assays using splenocytes and macrophages or other types of cells that express TLR9 receptors may be used to demonstrate that the CpG immunostimulatory oligonucleotide portion of the invention conjugate remains active after chemical conjugation. For example, in vitro assays using mouse splenocytes or J7-74 and J77743A mouse macrophages can be performed as described by Kandimalla et al. (Kandimilla et al., Bioconjug. Chem. (2002) 13:966-974). Briefly, splenocytes or J7-74 or J77743A cells are plated in 24 well dishes using $10^6$ cells/ml. CpG ODN alone (positive control) and the CpG conjugate is added at different equimolar concentrations (0.03 to 10.0 μg/ml) to the cell cultures. The cells are incubated at 37° C. for 24 hr and the supernatants collected for ELISA determination of secreted cytokines such as IL-12, IL-6, IFN-γ, and other pertinent cytokines and chemokines. Sandwich ELISAs are commercially available for such cytokines (see e.g., R&D Sciences, Minneapolis, Minn.).

Activity of invention conjugates can be demonstrated in tumor animal models such as tumor-bearing nude or BALB/c mice. Studies may include in vivo determination of pharmacokinetic clearance, biodistribution, imaging, and toxicity. In addition, the anti-tumor activity of each reagent can be studied in tumor-bearing mice by assessing their effects on tumor growth (tumor volume, survival times) and morphology. The tumor used for targeting needs to express the antigen or other agent to the antibody tumor targeting portion of the invention conjugate binds.

For example, $^{125}$I-labeled versions of the invention conjugates which comprise protein can be prepared using a modified chloramine-T method as described previously (Hornick et al., Cancer Biother. & Radiopharm. (1998) 13:225-226). Six-week-old BALB/c mice may be used to determine the whole-body pharmacokinetic clearance of all preparations. Briefly, groups of mice (n=5) previously fed potassium iodine in the drinking water for 1 wk to block thyroid uptake of radioiodine are administered i.v. injections of $^{125}$I-labeled conjugate (30-40 uCi/mouse). The whole-body activity immediately post-injection and at selected times thereafter is measured with a CRC-7 microdosimeter (Capintec, Inc., Pittsburgh, Pa.). The data are analyzed and half-life values will be determined as described previously (Hornick et al., Cancer Biother. & Radiopharm. (1998) 13:225-226; Homick et al., Clin. Cancer Res. (1999) 5:51-60).

Tissue biodistribution studies can be performed in tumor-bearing mice to evaluate the in vivo targeting ability of invention conjugates. For example, six-week-old BALB/c mice are injected subcutaneously with a 0.2 ml inoculum containing $1 \times 10^7$ tumor cells in the left flank. The tumors are grown for 7-10 days until they reach 0.5-1 cm in diameter. Within each group (n=5), individual mice are injected i.v. with a 0.1 ml inoculum containing 30-40 μCi of $^{125}$I-labeled conjugate. Animals are sacrificed by sodium pentobarbital overdose at 3 different time points post-injection (24, 48 and 72 h), and tissues are removed, weighed, and measured in a gamma counter. For each mouse, data is expressed as percentage injected dose/gram (% ID/g) and as tumor/organ ratio (cpm per gram tumor/cpm per gram organ). Significance levels are determined using the Wilcoxon's rank-sum test.

Invention conjugates also may be evaluated in vivo by radioimaging to assess tumor targeting potential. For example, groups of mice (n=5) with established tumors are given $^{131}$I-labeled conjugate (100-150 μCi/mouse) as described above. At various time points post-injection, the mice are anesthetized with a subcutaneous injection of 0.8 mg sodium pentobarbital and then imaged in a prone position with a Spectrum 91 gamma camera equipped with a pinhole collimator (Raytheon Medical Systems, Melrose Park, Ill.) set to record 10,000 counts using the Nuclear MAX Plus image analysis software package (MEDX Inc., Wood Dale, Ill.). The information from camera acquisition is used to calculate the percent of total body signal in the tumors. Pixel counts of tumor and non-tumor regions are obtained by drawing regions of interest with the computer to quantitate the efficacy of selected reagents in targeting tumor.

The maximum tolerated dose (MTD) of invention conjugates can be determined by standard methods. For example, groups of BALM mice (n=5) are injected intravenously with 5 daily consecutive doses with increasing concentrations of immunoconjugate (5 μg, 10 μg, 20 μg, 50 μg, 100 μg). Animals are observed for potential side effects such as weight loss, ruffled fur, lethargy, and loss of appetite.

The anti-tumor activity of invention conjugates may be compared with that of unconjugated tumor targeting agent, free CpG immunostimulatory oligonucleotide, and inactive CpG oligonucleotide containing conjugates to validate the efficacy of the conjugate. Preferably, the conjugate is more active per unit dose that either the antibody alone or the CpG immunostimulatory oligonucleotide alone, administered similarly. For example, the administered dose of each preparation per mouse is determined from the MTD data and efficacy is evaluated by monitoring tumor volume 3× per week as determined by caliper measurement performed in three dimensions. Regression or inhibition of growth relative to the controls indicates efficacy of the therapy. For these studies, different tumor models may be used. Groups of tumor-bearing mice (n=8) receive intravenous treatment 7-10 days after tumor implantation for 5 consecutive days with MTD doses determined by the toxicity studies described above. This treatment regimen is similar to others previously used to study cytokine and chemokine immunoconjugates of the chTNT-3 antibody (Hornick et al., Clin. Cancer Res. (1999) 5:51-60). All doses are administered in a 0.1 ml inoculum by the same person to maintain consistency. If a particular preparation is found effective, the minimal optimal dose and the fewest number of doses is determined using alternative treatment regimens such as 1, 2, or 3 times per week for one or two courses. These data are analyzed to determine if the dosing schedule correlates with the pharmacokinetic and the biodistribution data obtained for that reagent. Animal survival times are recorded and those mice with tumors larger than 2 cm in diameter are sacrificed according to established humane vivarium protocols. Statistical analysis is performed using the Wilcoxin's rank sum test to obtain P values.

Morphological analysis and immunohistochemical evaluation of tumor samples can be used to identify the effects of invention conjugates. For example, tumor samples removed at 1, 3, 5, and 7 days after the completion of a single course of therapy (5 daily injections) are either fixed overnight in 10% neutral buffered formalin for paraffin embedding or snap frozen submerged in O.C.T. compound to prepare samples for frozen sectioning. Paraffin embedded sections are stained with H & E for morphological examination and frozen sections are used for immunohistochemical studies using a panel of anti-sera specific for lymphoid subsets. Exemplary primary antibodies used in immunohistochemical studies and their working dilutions are shown below in Table 2. Similar antibody reagents are available for detecting human lymphocyte subsets. Frozen sections are stained for the presence of cytokines and tumor vessel antigens (IL-2, TNFα, IFN-γ, IL-10, TGFβ, and selected adhesion molecules) induced in the tumor by treatment using appropriate antisera. For all these studies, non-treated tumors are used in parallel.

TABLE 2

Panel of Immunochemical Reagents for Staining Murine Lymphocyte Subsets.

| Monoclonal Antibodies (BD PharMingen) | Titration | Lymphocyte subset |
|---|---|---|
| Anti-CD3e | 1:50 | Mature T cells and thymocytes |
| Anti-CD4 | 1:25 | MHC class II - restricted T cells and most thymocytes |
| Anti-CD8a | 1:100 | MHC class I - restricted T cells |
| Anti-Panendothelial | 1:100 | Endothelial cells |
| Anti-CD11b | 1:100 | Granulocytes, macrophages, dendritic cells, NK cells |
| Anit-CD11c | 1:100 | Dendritic cells and CD4$^+$CD8$^+$ T-cells |
| Anti-Pan NK | 1:100 | NK cells (~90%) |
| Anti-CD19 | 1:20 | B-cell (pre-B cell through mature B-cell) |
| Anti-ly6G | 1:200 | Neutrophils |

Cytokines/chemokines induced in the tumor or in draining lymph nodes by invention conjugates may be determined by real-time PCR. For example, tumors and tumor draining lymph nodes (TDLN) are removed at days 0, 3, 6, 9, 12, 15 after the initiation of treatment. Total RNA is extracted by Trizol (Gibco, Rockville, Md.) and 1 μg of total RNA is reverse transcribed into cDNA by a first-strand cDNA synthesis kit (Invitrogen Life technologies, CA). The PCR reaction mixture consists of 5 μl of cDNA, 10 μl of SYBR green master Mix (Applied Biosystems, Foster Calif.), 2 μl of primers (3.3 μM) and 1 μl of water. PCR is performed for 30 cycles. The quantity of cytokines (IL-2, IL-10, IL-4, IFN-γ, TGF-β1, and TNFα) is detected by an ABI PRISM® 7900HT Sequence Detection System (Applied biosystems, Foster, Calif.). Exemplary DNA primers that can be used to detect cytokines/chemokines is shown in Table 3. Primers for detecting human versions of these cytokines are well known in the art.

TABLE 3

DNA Primers for Real-Time PCR Studies.

| | Forward (SEQ ID Nos 17-23) | Reverse SEQ ID Nos 24-30) |
|---|---|---|
| IL-2 | TGA CAA CAC ATT TGA GTG CCA AT | GAA GGC TAT CCA TCT CCT CAG AAA |
| IFNγ | CAG CAA CAG CAA GGC GAA CTG GTT GAC | GAC CTG TGG GTT |
| TNFα | CAT CTT CTC AAA ATT CGA TGG GTG ACAA | GAG TAG ACA AGG TAC AAC CC |
| IL-4 | ACA GGA GAA GGG ACG CCA GAA T | GCC CTA CAG ACG AGC TCA |
| IL-10 | GGT TGC CAA GCC TTA TCG ACC GA | TGC TCC ACT GCC TTG CT |
| TGFβ1 | TGA CGT CAC TGG AGT TGT GGT ACG G | TCA TGT CAT GGA TGG TGC |

TABLE 3-continued

DNA Primers for Real-Time PCR Studies.

| | Forward (SEQ ID Nos 17-23) | Reverse SEQ ID Nos 24-30) |
|---|---|---|
| HPRT | AGC TAC TGT AAT GAT CAG TCA ACG | AGA GGT CCT TTT CAC CAG CA |

Lymphocyte subset infiltration and intracellular cytokine expression analyzed by flow cytometry (i.e. FACS) can be used to evaluate the in vivo biological effects of invention conjugates. For example, tumors and TDLNs are removed on days 0, 3, 6, 9, 12, 15 after the initiation of treatment and cut into 2-3 mm pieces in a culture petri dish. The tissues are digested with 0.01% DNAse, 0.01% hyaluranidase, and 0.1% collagenase for 2-3 hr at 37° C. with continuous stirring. The resulting single cell suspensions are washed twice with 0.1% FCS in PBS and stained by standard flow cytometry methods. Subpopulations of lymphocytes infiltrating the tissues are identified by staining with conjugated antibodies including PE-anti-CD4, FITC-anti-CD8, PE-anti-PMN, FITC-anti-CD25, and FITC-anti-NK1.1 (BD Biosciences PharMingen, San Diego, Calif.). To measure intracellular cytokine expression, cells are stained directly, or non-specifically stimulated for 4 hr with 5 ng/ml PMA (Sigma Aldrich, St. Louis, Mo.) and 500 ng/ml ionomycin in the presence of GolgiStop (BD PharMingen, San Diego, Calif.). Samples may also be stimulated specifically with tumor lysates for 4-6 hr in the presence of GolgiStop. T-cells are then stained for surface markers (CD45$^+$ or CD8$^+$) and for presence of cytokines using anti-cytokine antibodies. Briefly, single cell suspensions are reacted with CD16 (BD PharMingen, San Diego, Calif.) for 15 min at 4° C. to block mouse Fc receptors. The cells are washed and incubated for 30 min either with FITC-CD45$^+$ to stain total lymphocytes or PE-anti-CD8$^+$ for CD8$^+$ T-cells. Cells are fixed and permeabilized with 100 μl Cytofix/Cytoperm (BD PharMingen, San Diego, Calif.) for 15 min, washed with 300 μl of Perm/Wash, resuspended in 50 μl Perm/Wash with anti-IL-2, anti-IFN-γ, or anti-TNFα for 30 min in the dark. Binding of antibody to the cells is determined by FACS analysis.

The invention conjugates described herein can be used for treatment of cancer in an individual so afflicted. Accordingly, the present invention includes a method of reducing the size of a tumor or inhibiting the growth of cancer in an individual comprising administering an effective amount of the invention conjugates.

A further aspect of the invention is a method of inhibiting the development of metastasis in an individual suffering from cancer, comprising administering an effective amount of the invention conjugates.

Reducing the activity of immunoregulatory T cells in an individual as part of the methods of the invention may be achieved by removing ex vivo or by depleting or inactivating immunoregulatory T cells in the individual. The term "immunoregulatory T cells" as used herein refers to a population of T cells that function, directly or indirectly, to suppress the host anti-tumor immune response. Immunoregulatory T cells may be CD4+, CD25+ or positive for both markers.

The term "removing ex vivo" as used herein with reference to immunoregulatory T cells means that immunoregulatory T cells are removed from the circulation of an individual by an ex vivo method such as flow cytometric cell separation, column or filter separation, and the like. The column or filter may have bound thereto an antibody that can bind to immunoregulatory T cells. Antibodies that bind to immunoregulatory T cells also may be used to identify such cells for removal by a flow cytometric device. Antibody suitable for binding to immunoregulatory T cells include antibody specific for the CD4 antigen, the alpha chain subunit of the IL-2 receptor (i.e. CD25), and the like. A combination of such anti-T cell antibodies also may be used. Daclizumab®, a humanized monoclonal antibody that binds to CD25 or Basiliximab®, a chimeric version of this same antibody is commercially available from Novartis Pharma AG. Hu-Max-CD4®, a fully humanized antibody against CD4 has been made (GenMab). CD4 antibody is described by North and Awwad 1990, while CD25 is described by Onizuka et al. 1999.

The term "depleting or inactivating in vivo immunoregulatory T cells" as used herein refers to a reduction in the number or functional capability of immunoregulatory T cells which suppress the host anti-tumor immune response that occurs following administration of a pharmaceutical agent to the host. The pharmaceutical agent is one that when administered causes a loss of immunoregulatory T cells (i.e., depletion) or inactivation of anti-tumor immune suppression function of the immunoregulatory T cells. The ultimate result of such treatment is to reduce immunoregulatory T cell activity in the recipient of the treatment.

Depleting or inactivating immunoregulatory T cells may be achieved by administering a pharmaceutical agent such as an antibody specific for the CD4 antigen, the alpha chain subunit of the IL-2 receptor (i.e. CD25), and the like, as described above. Also, an antibody to gamma delta immunoregulatory T cells can be used to deplete such cells and stimulate anti-tumor immunity as described previously. Seo et al., J. Immunol. (1999) 163:242-249. Anti-CD40 ligand, also may be used to deplete or inactivate immunoregulatory T cells.

Partial antibody constructs such as CTLA4Ig, a fusion protein of CTLA-4 and Fc of immunoglobulin (Ig) heavy chain, can be used to inhibit the essential co-stimulatory signal for full T cell activation via blocking the interaction between CD28 and B7 molecules. CTLA4Ig may be administered as a pharmaceutical to render regulatory T cells nonresponsive (i.e. inactivation). See Park et al. Pharm Res. (2003) 20(8):1239-48. An IL-2 fusion to pseudomonas exotoxin (OnTac) is yet another agent for depleting or inactivating regulatory T cells.

In another approach, agents may be administered that prevent the induction of CD8+ cytolytic T-lymphocyte (CTL) tumor anergy. Agents that agonize CD137, such as agonistic antibodies, may be used to restore the tumor cytolytic function of established anergic CTLs upon reencountering their cognate antigen. See Wilcox et al., Blood (2004) 103:177-184. This approach can be used to break T-cell tolerance to tumor antigens.

Agents that agonize glucocorticoid-induced tumor necrosis factor receptor (GITR) ligand on CD4/CD25+ immunoregulatory T cells reverses the suppressive action of these cells. GITR ligand agonists are described in Tone et al., PNAS (2003) 100:15059-15064; Stephens et al. 2004 and Shimizu et al. 2002).

Antibodies to neuropilin (e.g. Bruder et al. 2004) and antibodies to CTLA-4 (e.g. Leach et al. 1996) also can be administered in vivo to deplete immunoregulatory T cells or reduce their activity.

Methods of removing, depleting or inactivating immunoregulatory T cells may be used even if the methods are not limited solely to such cells. Effort to remove, deplete or inactivate immunoregulatory T cells may be performed multiple times during a given period of treatment. Also, different methods may be used together (e.g., ex vivo cell removal and in vivo depletion or inactivation). The amount of anti-T cell antibody administered for depletion or inactivation may be similar to the amount used in the transplantation field. See, e.g., Meiser et al., Transplantation. (1994) 27; 58(4): 419-23.

Immunoregulatory T cells may be removed, depleted or inactivated before, during and/or after administration of the invention conjugates. Immunoregulatory T cells are preferably removed, depleted or inactivated before administering the invention conjugates.

In a further embodiment, the invention methods for cancer therapy may include adoptive transfer of immune cells to enhance anti-tumor immunity. As used herein "adoptive transfer" refers to the administration of immune cells, from another individual or from the same individual. These are preferably T cells, which may be activated ex vivo to enhance their ability to function in supporting an anti-tumor immune response. Adoptively transferred immune cells may be activated ex vivo by any of a variety of well known agents including, for example, exposure to IL-2 and/or to anti-CD3 antibodies. Ex vivo activation also may include exposure to a cancer cell vaccine. Such cancer cell vaccine may constitute live (but non-replicating), or killed cancer cells from the individual to be treated or from another cancer entirely. The vaccine also may be a cancer cell extract or purified vaccine preparation derived from cancer cells. Cancer cell vaccines are well known in the art and may be prepared in accordance with well known methods.

In this form of therapy, patients receive multiple infusions of T-cells after ex vivo stimulation with IL-2 (Lum, et al., J Immunother. (2001) 24:408-19) or other agents such as anti-CD3+ and anti-CD28+ antibodies (June, C. H.: J. Immunother (2001) 24(5): 389-391).

Compounds described herein can be administered as a pharmaceutical or medicament formulated with a pharmaceutically acceptable carrier. Accordingly, the compounds may be used in the manufacture of a medicament or pharmaceutical composition. Pharmaceutical compositions of the invention may be formulated as solutions or lyophilized powders for parenteral administration. Powders may be reconstituted by addition of a suitable diluent or other pharmaceutically acceptable carrier prior to use. Liquid formulations may be buffered, isotonic, aqueous solutions. Powders also may be sprayed in dry form. Examples of suitable diluents are normal isotonic saline solution, standard 5% dextrose in water, or buffered sodium or ammonium acetate solution. Such formulations are especially suitable for parenteral administration, but may also be used for oral administration or contained in a metered dose inhaler or nebulizer for insufflation. It may be desirable to add excipients such as polyvinylpyrrolidone, gelatin, hydroxy cellulose, acacia, polyethylene glycol, mannitol, sodium chloride, sodium citrate, and the like.

Alternately, compounds may be encapsulated, tableted or prepared in an emulsion or syrup for oral administration. Pharmaceutically acceptable solid or liquid carriers may be added to enhance or stabilize the composition, or to facilitate preparation of the composition. Solid carriers include starch, lactose, calcium sulfate dihydrate, terra alba, magnesium stearate or stearic acid, talc, pectin, acacia, agar or gelatin. Liquid carriers include syrup, peanut oil, olive oil, saline and water. The carrier may also include a sustained release material such as glyceryl monostearate or glyceryl distearate, alone or with a wax. The amount of solid carrier varies but, preferably, will be between about 20 mg to about 1 g per dosage unit. The pharmaceutical preparations are made following the conventional techniques of pharmacy involving milling, mixing, granulating, and compressing, when necessary, for tablet forms; or milling, mixing and filling for hard gelatin capsule forms. When a liquid carrier is used, the preparation may be in the form of a syrup, elixir, emulsion, or an aqueous or non-aqueous suspension. For rectal administration, the invention compounds may be combined with excipients such as cocoa butter, glycerin, gelatin or polyethylene glycols and molded into a suppository.

Compounds may be formulated to include other medically useful drugs or biological agents. The compounds also may be administered in conjunction with the administration of other drugs or biological agents useful for the disease or condition to which the invention compounds are directed.

As employed herein, the phrase "an effective amount," refers to a dose sufficient to provide concentrations high enough to impart a beneficial effect on the recipient thereof. The specific therapeutically effective dose level for any particular subject will depend upon a variety of factors including the disorder being treated, the severity of the disorder, the activity of the specific compound, the route of administration, the rate of clearance of the compound, the duration of treatment, the drugs used in combination or coincident with the compound, the age, body weight, sex, diet, and general health of the subject, and like factors well known in the medical arts and sciences. Various general considerations taken into account in determining the "therapeutically effective amount" are known to those of skill in the art and are described, e.g., in Gilman et al., eds., Goodman And Gilman's: The Pharmacological Bases of Therapeutics, 8th ed., Pergamon Press, 1990; and Remington's Pharmaceutical Sciences, 17th ed., Mack Publishing Co., Easton, Pa., 1990. Dosage levels typically fall in the range of about 0.001 up to 100 mg/kg/day; with levels in the range of about 0.05 up to 10 mg/kg/day are generally applicable. A compound can be administered parenterally, such as intravascularly, intravenously, intraarterially, intramuscularly, subcutaneously, or the like. Administration can also be orally, nasally, rectally, transdermally or inhalationally via an aerosol. The compound may be administered as a bolus, or slowly infused.

A therapeutically effective dose can be estimated initially from cell culture assays by determining an IC50. A dose can then be formulated in animal models to achieve a circulating plasma concentration range that includes the IC50 as determined in cell culture. Such information can be used to more accurately determine useful initial doses in humans. Levels of drug in plasma may be measured, for example, by HPLC. The exact formulation, route of administration and dosage can be chosen by the individual physician in view of the patient's condition.

The administration of the cancer therapeutic agent (invention conjugate) to an immunocompetent individual may result in the production of antibodies against the agents. Reducing the immunogenicity of the invention cancer therapeutic agents can be addressed by methods well known in the art such as by attaching long chain polyethylene glycol (PEG)-based spacers, and the like, to the agent. Long chain PEG and other polymers are known for their ability to mask foreign epitopes, resulting in the reduced immunogenicity of therapeutic proteins that display foreign epitopes (Katre et al., J. Immunol. (1990,) 144, 209-213; Francis et al., Int. J. Hematol. (1998) 68, 1-18). Alternatively, or in addition, the individual administered the cancer therapeutic agents or compositions may be administered an immunosuppressent such as cyclosporin A, anti-CD3 antibody, and the like.

The following examples serve to illustrate the present invention. These examples are in no way intended to limit the scope of the invention.

EXAMPLES

Example 1

Generation of CpG Immunostimulatory Oligonucleotide Linked chTNT-3 Immunoconjugates Chimeric TNT-3 antibody was produced according to published results (Hornick et al., Cancer Biother. & Radiopharm. (1998) 13:255-268). cTNT-3 was incubated with the cross-linker N-[ε-Maleimidocaproyloxy]sulfosuccinimide ester (Sulfo-EMCS; Pierce, Ill.) in a 100 mM EDTA-PBS buffer solution (pH 8.3) at a molar ratio of 1:20 for 1 h at room temperature.

Phosphothioate backbone CpG ODN modified with sulfhydral group at the terminal nucleotide (see FIG. 1), was custom synthesized by Norris Cancer Center Microchemical Core Facility (Los Angeles, Calif.). The phosphothioated sulfhydryl-modified ODN 1826 (SEQ ID NO:1) comprised a CpG motif with the sequence 5'-S-TCCATGACGTTCCT-GACGTT-3'. Phosphothioated sulfhydryl-modified ODN 1745 (SEQ ID NO 14), used as a negative control, 5'-S-TCCAATGAGCTTCCTGAGTCT-3' for CpG activity along with Phosphothioated sulfhydryl-modified ODN 2006 (SEQ ID NO: 5), 5'-TCGTCGTTTTGTCGTTTTGTCGTT-3', which is B cell specific.

Sulfhydryl-modified ODN were activated by reducing in a 50 mM DTT-EDTA-PBS solution for 2 h at room temperature. Subsequently, unbound Sulfo-EMCS and DTT were removed from the respective solutions by chromatography using a PD-10 column.

Activated ODN were incubated overnight with the linker-modified chTNT-3 (sulfo-EMCS/chTNT-3) at a molar ratio of 10:1 at 4° C. and thereafter L-cysteine was added to quench reactive Sulfo-EMCS. Free ODN was removed by centrifugation on a Centricon-100. Purified conjugate was analyzed on a 4-15% gradient reducing SDS-PAGE and consecutively visualized with coomassie-blue stain. The ratio of bound CpG ODN on chTN-3 was determined spectrophotometrically and calculated as OD260/OD280 ratio using the method of Ngo and Oliva (protocol according to TriLink BioTechnologies, La Jolla, Calif.). The batches of CpG/chTNT-3 immunoconjugates used in this study had a ratio of about 1.5 CpG molecules linked to one chTNT-3 molecule.

Example 2

In Vitro Conjugate Immunoreactivity

CpG/chTNT-3 preparations were radiolabeled with $^{125}$I using a modified chloramine-T method. Immunoreactivity was evaluated by a conventional fixed Raji cell radioimmunoassay. Briefly, Raji lymphoma cells (ATCC: Rockville, Md.) were resuspended in freshly prepared 2% paraformaldehyde in PBS to fix the cells and cause disruption of the cell membrane. Radioiodinated immunoconjugates (approximately 100,000 cpm/tube) were then incubated in triplicate with $10^6$ fixed Raji cells for 1 h. Both the chTNT-3 parental antibody and chTNT-3/CpG immunoconjugates showed immunoreactivities of 70% or greater.

The biological activity of the CpG motif in the immunoconjugates was assessed using the murine macrophage cell lines J7-74 and J77743A, available from the ATCC (Rockville, Md.) as described by Kandimalla et al. Bioconjug. Chem. (2002) 13:966-974. Briefly, cells were plated in 24 well dishes using $10^6$ cells/ml. CpG alone (positive control) and the CpG/chTNT-3 immunoconjugates were added at equimolar concentrations of 0.1, 0.3, 1.0, or 3.0 μg/ml to the cell cultures. The cells are then incubated at 37° C. for 24 hr and the supernatants collected for IL-6 determination using a commercial sandwich ELISA assay from R&D Sciences (Minneapolis, Minn.). Results were interpolated from the standard curves.

Figure 2:
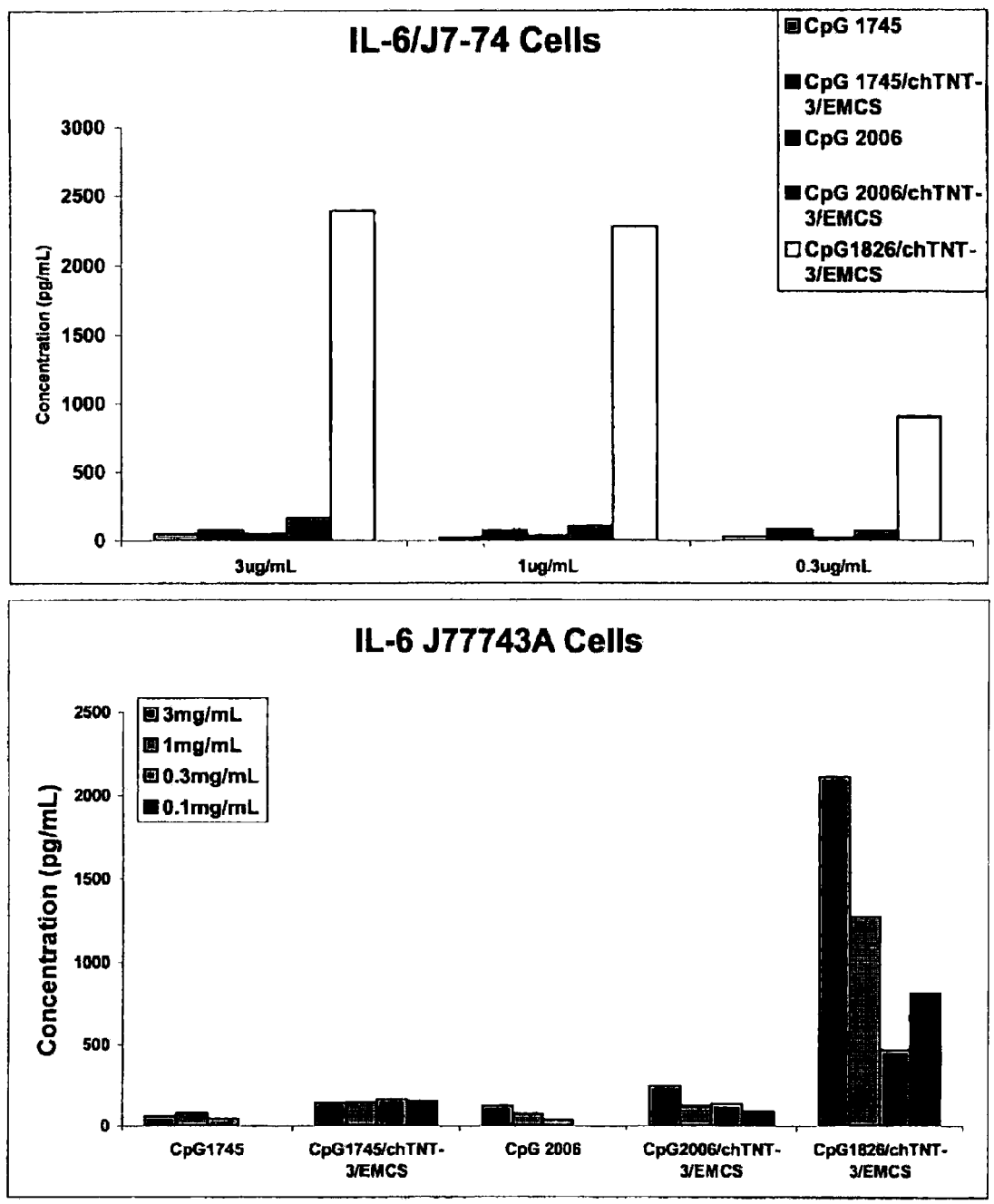
FIG. 2 demonstrates the induction of IL-6 secretion in (A) J7-74 and (B) J77743A cells after incubation with increasing concentrations of chTNT-3/CpG immunoconjugates. The CpG 1826 immunoconjugate was able to induce the secretion of IL-6 in the J7 cell lines.

As seen in FIG. 2, both cell lines showed a dose dependent induction of IL-6 secretion after incubation with chTNT-3/CpG 1826 motif. Other immunoconjugates were negative in this assay including control immunoconjugate CpG 1745 and CpG 2006, which is specific for B-lymphocytes.

Example 3

In Vivo CpG Immunostimulatory Oligonucleotide Immunoconjugate Cancer Therapy Evaluation In vivo cancer therapy studies were performed in tumor-bearing BALB/c mice. Groups of mice (n=5) were transplanted with the Colon 26 colon carcinoma in the left flank by the injection of $5 \times 10^6$ cells subcutaneously using a 0.2 ml inoculum. When the tumors reached 0.5 cm in diameter, treatment was initiated and consisted of 4 daily intravenous injections of chTNT-3/CpG (1826) or control chTNT-3 for each group. In addition, one group was treated with 4 daily intratumoral injections of unconjugated CpG 1826. Tumor volumes were calculated every other day by caliper measurement.

Figure 3:
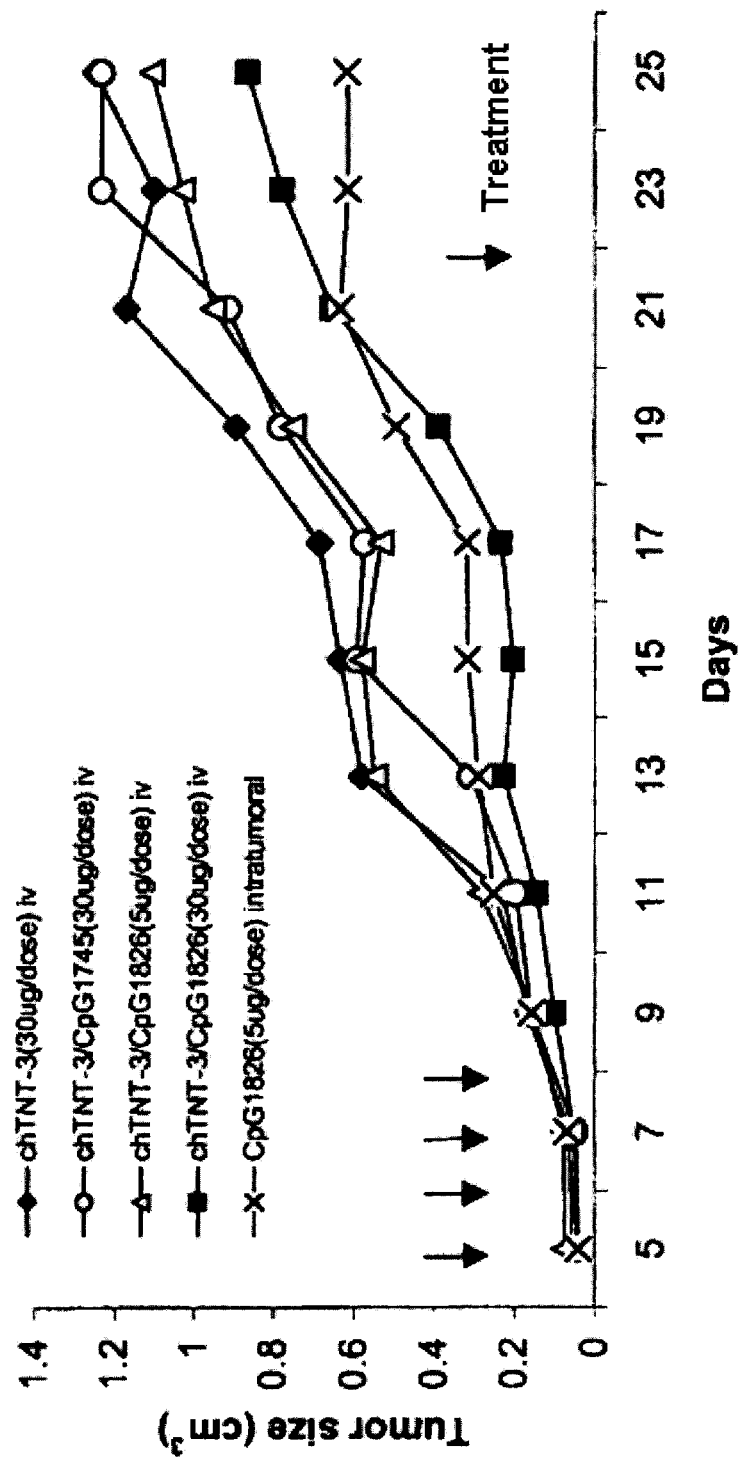
FIG. 3 shows immunotherapy of Colon 26 tumor bearing BALB/c mice following administration of CpG and chTNT-3/CpG immunoconjugates.

As shown in FIG. 3, tumor reduction of about 50% was observed at day 21 post-treatment in the chTNT-3/CpG 1826 group compared to control treated mice. The amount of tumor reduction by chTNT-3/CpG 1826 at a 30 ug dose was comparable to that achieved with the 5 ug intratumoral administration of free CpG 1826 even though this dose represented about ⅓ as much CpG as the intratumoral injection. By contrast, those groups of mice receiving intravenous control parental antibody or chTNT-3/CpG 1745 had similar growth curves demonstrating inactivity for this conjugate.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising," "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims. Other embodiments are set forth within the following claims.

What is claimed is:

1. A cancer therapeutic agent comprising a tumor necrosis therapy (TNT) cancer antibody specific for an intranuclear antigen covalently linked by a linker to an oligonucleotide comprising an immunostimulatory sequence motif which contains at least one unmethylated CG dinucleotide, wherein the linker comprises a heterobifunctional linker.

2. The cancer therapeutic agent of claim 1, wherein said antibody is humanized.

3. The cancer therapeutic agent of claim 1, wherein said antibody is selected from the group consisting of: a dimer of Fab, a Fab' monomer, and a single chain Fv ("scFv") polypeptide.

4. The cancer therapeutic agent of claim 1, wherein said antibody binds to the necrotic area of a tumor.

5. The cancer therapeutic agent of claim 1, wherein said antibody is NHS76.

6. The cancer therapeutic agent of claim 1, wherein said immunostimulatory sequence motif of said oligonucleotide is TCGTT or TCGTA or both.

7. The cancer therapeutic agent of claim 1, wherein said cancer antibody is linked to multiple oligonucleotides that comprise an immunostimulatory sequence motif which contains at least one unmethylated CG dinucleotide.

8. The cancer therapeutic agent of claim 1 wherein said immunostimulatory sequence motif of said oligonucleotide binds to human Toll-Like Receptor 9.

9. The cancer therapeutic agent of claim 1, wherein said oligonucleotide contains multiple immunostimulatory sequence motifs.

10. The cancer therapeutic agent of claim 1, wherein said oligonucleotide comprises a phosphothioate linkage.

11. The cancer therapeutic agent of claim 1, wherein said heterobifunctional linker is selected from the group consisting of: Sulfosuccinimidyl 4-[N-maleimidomethyl]cyclohexane-1-carboxylate, N-[ε-Maleimidocaproyloxy]sulfosuccinimide ester, m-Maleimidobenzoyl-N-hydroxysulfosuccinimide ester, N-[κ-Maleimidoundecanoyloxy]sulfosuccinimide ester, N-[β-Maleimidopropionic acid] Hydrazide·TFA, N-[β-Maleimidopropyloxy] succinimide ester, N-[γ-Maleimidobutyryloxy]sulfosuccinimide ester, Sulfosuccinimidyl 4-[p-maleimidophenyl]butyrate, and Succinimidyl 4-[p-maleimidophenyl]butyrate.

12. A cancer therapeutic agent of claim 1 further comprising a pharmaceutically acceptable carrier.

\* \* \* \* \*